(12) United States Patent
Biggie et al.

(10) Patent No.: US 7,520,872 B2
(45) Date of Patent: Apr. 21, 2009

(54) CLOSED WOUND DRAINAGE SYSTEM

(75) Inventors: John J. Biggie, Lighthouse Point, FL (US); Lydia B. Biggie, Lighthouse Point, FL (US); John A. Dawson, Dallastown, PA (US)

(73) Assignee: NeoGen Technologies, Inc., Coral Springs, FL (US)

( * ) Notice: Subject to any disclaimer, the term of this patent is extended or adjusted under 35 U.S.C. 154(b) by 210 days.

(21) Appl. No.: 10/909,222

(22) Filed: Jul. 30, 2004

(65) Prior Publication Data

US 2005/0137539 A1   Jun. 23, 2005

Related U.S. Application Data

(63) Continuation-in-part of application No. 10/243,004, filed on Sep. 13, 2002, now Pat. No. 6,979,324.

(60) Provisional application No. 60/481,977, filed on Jan. 30, 2004, provisional application No. 60/481,165, filed on Jul. 31, 2003.

(51) Int. Cl.
  *A61F 13/00* (2006.01)
  *A61M 1/00* (2006.01)
  *A61M 27/00* (2006.01)
  *A61H 7/00* (2006.01)

(52) U.S. Cl. .................. 604/319; 604/313; 604/543; 604/305; 601/6

(58) Field of Classification Search .......... 604/289, 604/290, 304, 305, 313, 315, 316, 540, 543, 604/317, 319, 322, 327, 332, 334, 336, 356; 601/6–14

See application file for complete search history.

(56) References Cited

U.S. PATENT DOCUMENTS

| | | |
|---|---|---|
| 765,746 A | 7/1904 | Miner |
| 843,674 A | 2/1907 | Funk |
| 1,355,679 A | 10/1920 | McConnell |
| 1,355,846 A | 10/1920 | Bannells |
| 1,385,346 A | 7/1921 | Taylor |

(Continued)

FOREIGN PATENT DOCUMENTS

DE           561757           10/1932

(Continued)

OTHER PUBLICATIONS

Author Unknown, "The Not-So-Bald-Truth", Science, Sep. 1992, p. 42 (1 page).

(Continued)

*Primary Examiner*—Tatyana Zalukaeva
*Assistant Examiner*—Michael G Bogart
(74) *Attorney, Agent, or Firm*—Nixon Peabody LLP

(57) ABSTRACT

A portable closed wound drainage system that uses a pouch shaped dressing which is inserted into a wound. At least a portion of the outer surface of the pouch 1 is porous to allow exudates to enter. Exudates are removed from the pouch by flexible tubing which is secured inside the pouch at one end, and secured at the other end to a portable drain/suction unit. The pouch contains porous material, and may optionally contain beads and fillers which are antibacterial in nature. The tubing can have a single or multi-lumen structure with perforations in the side walls of the end of the tube that is inserted in the pouch to allow body fluids to enter laterally. The portable drain/suction unit is preferably a portable battery powered device. The pouch and the tube are sealed by a flexible sealing material which is applied to the outer surface of the skin around the periphery of the pouch and the tubing as it exits the pouch. This sealing material is preferably a hydrocolloid, a silicone, or a lyogel, such as a hydrogel, which are easily deformable. A cosmetic cover sheet is attached to the patient's skin over the closed wound drainage system.

41 Claims, 22 Drawing Sheets

U.S. PATENT DOCUMENTS

| | | | |
|---|---|---|---|
| 2,232,254 A | 2/1941 | Morgan | |
| 2,280,915 A | 4/1942 | Johnson | |
| 2,338,339 A | 1/1944 | Mere et al. | |
| 2,547,758 A | 4/1951 | Keeling | |
| 2,969,057 A | 1/1961 | Simmons | |
| 3,026,526 A | 3/1962 | Montrose | |
| 3,026,874 A | 3/1962 | Stevens | |
| 3,042,041 A | 7/1962 | Jascalevich | |
| 3,367,332 A | 2/1968 | Groves | |
| 3,478,736 A | 11/1969 | Roberts et al. | |
| 3,481,326 A | 12/1969 | Schamblin | |
| 3,486,504 A | 12/1969 | Austin, Jr. | |
| 3,520,300 A | 7/1970 | Flower, Jr. | |
| 3,568,675 A | 3/1971 | Harvey | |
| 3,572,340 A * | 3/1971 | Lloyd et al. | 604/133 |
| 3,610,238 A | 10/1971 | Rich, Jr. | |
| 3,648,692 A | 3/1972 | Wheeler | |
| 3,682,180 A | 8/1972 | McFarlane | |
| 3,809,087 A | 5/1974 | Lewis, Jr. | |
| 3,826,254 A | 7/1974 | Mellor | |
| 3,874,387 A | 4/1975 | Barbieri | |
| 3,896,810 A | 7/1975 | Akiyama | |
| 3,908,664 A | 9/1975 | Loseff | |
| 3,954,105 A | 5/1976 | Nordby et al. | |
| 3,993,080 A | 11/1976 | Loseff | |
| RE29,319 E | 7/1977 | Nordby et al. | |
| 4,080,970 A | 3/1978 | Miller | |
| 4,096,853 A | 6/1978 | Weigand | |
| 4,112,947 A | 9/1978 | Nehring | |
| 4,139,004 A | 2/1979 | Gonzalez, Jr. | |
| 4,149,541 A | 4/1979 | Gammons et al. | |
| 4,165,748 A | 8/1979 | Johnson | |
| 4,169,563 A | 10/1979 | Leu | |
| 4,172,455 A | 10/1979 | Beaussant | |
| 4,182,343 A | 1/1980 | Inaba | |
| 4,224,945 A | 9/1980 | Cohen | |
| 4,250,882 A | 2/1981 | Adair | |
| 4,261,363 A | 4/1981 | Russo | |
| 4,275,721 A | 6/1981 | Olson | |
| 4,297,995 A | 11/1981 | Golub | |
| 4,333,468 A | 6/1982 | Geist | |
| 4,373,519 A | 2/1983 | Errede | |
| 4,382,441 A | 5/1983 | Svedman | |
| 4,392,853 A | 7/1983 | Muto | |
| 4,419,097 A | 12/1983 | Rowland | |
| 4,468,227 A | 8/1984 | Jensen | |
| 4,469,092 A | 9/1984 | Marshall et al. | |
| 4,475,909 A | 10/1984 | Eisenberg | |
| 4,480,638 A | 11/1984 | Schmid | |
| 4,525,166 A | 6/1985 | Leclerc | |
| 4,527,064 A | 7/1985 | Anderson | |
| 4,533,352 A | 8/1985 | Van Beek et al. | |
| 4,543,100 A | 9/1985 | Brodsky | |
| 4,551,139 A | 11/1985 | Plaas et al. | |
| 4,553,967 A | 11/1985 | Ferguson et al. | |
| 4,569,348 A | 2/1986 | Hasslinger | |
| 4,571,520 A | 2/1986 | Saito et al. | |
| 4,573,965 A | 3/1986 | Russo | |
| 4,578,065 A * | 3/1986 | Habib | 604/336 |
| 4,605,399 A | 8/1986 | Weston et al. | |
| 4,608,041 A | 8/1986 | Nielsen | |
| 4,624,656 A | 11/1986 | Clark et al. | |
| 4,640,688 A | 2/1987 | Hauser | |
| 4,733,659 A | 3/1988 | Edenbaum et al. | |
| 4,743,232 A | 5/1988 | Kruger | |
| 4,759,354 A | 7/1988 | Quarfoot | |
| 4,764,167 A | 8/1988 | Tu | |
| 4,765,316 A | 8/1988 | Marshall | |
| 4,775,909 A | 10/1988 | Inoue et al. | |
| 4,778,456 A | 10/1988 | Lokken | |
| 4,813,094 A | 3/1989 | Krotine | |
| 4,820,265 A | 4/1989 | DeSatnick et al. | |
| 4,820,284 A | 4/1989 | Hauri | |
| 4,834,110 A | 5/1989 | Richard | |
| 4,836,192 A | 6/1989 | Abbate | |
| 4,838,883 A | 6/1989 | Matsuura | |
| 4,840,187 A | 6/1989 | Brazier | |
| 4,851,545 A | 7/1989 | Song et al. | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,917,112 A | 4/1990 | Kalt | |
| 4,919,654 A | 4/1990 | Kalt | |
| 4,921,492 A | 5/1990 | Schultz et al. | |
| 4,925,447 A | 5/1990 | Rosenblatt | |
| 4,931,519 A | 6/1990 | Song et al. | |
| 4,936,834 A | 6/1990 | Beck et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,969,881 A | 11/1990 | Viesturs | |
| 4,985,019 A | 1/1991 | Michelson | |
| 5,035,884 A | 7/1991 | Song et al. | |
| 5,037,397 A | 8/1991 | Kalt et al. | |
| 5,045,075 A | 9/1991 | Ersek | |
| 5,086,764 A | 2/1992 | Gilman | |
| 5,100,396 A | 3/1992 | Zamierowski | |
| 5,106,362 A | 4/1992 | Gilman | |
| 5,113,871 A | 5/1992 | Viljanto et al. | |
| 5,149,331 A | 9/1992 | Ferdman et al. | |
| 5,228,431 A | 7/1993 | Giarretto | |
| 5,240,862 A | 8/1993 | Koenhen et al. | |
| 5,261,893 A | 11/1993 | Zamierowski | |
| 5,279,010 A | 1/1994 | Ferrand et al. | |
| 5,298,015 A | 3/1994 | Komatsuzaki et al. | |
| 5,358,494 A | 10/1994 | Svedman | |
| 5,370,610 A | 12/1994 | Reynolds | |
| D364,679 S | 11/1995 | Heaton et al. | |
| 5,527,293 A | 6/1996 | Zamierowski | |
| 5,540,412 A | 7/1996 | Doll | |
| 5,549,584 A | 8/1996 | Gross | |
| 5,618,275 A | 4/1997 | Bock | |
| 5,624,419 A | 4/1997 | Ersek et al. | |
| 5,636,643 A | 6/1997 | Argenta et al. | |
| 5,643,229 A | 7/1997 | Sinaiko | |
| 5,645,081 A | 7/1997 | Argenta et al. | |
| 5,656,588 A | 8/1997 | Zaloga et al. | |
| 5,664,270 A | 9/1997 | Bell et al. | |
| 5,678,564 A | 10/1997 | Lawrence et al. | |
| 5,685,859 A | 11/1997 | Kornerup | |
| 5,686,303 A | 11/1997 | Korman | |
| 5,840,049 A | 11/1998 | Tumey et al. | |
| D406,899 S | 3/1999 | Cottle | |
| 5,891,111 A | 4/1999 | Ismael | |
| 5,906,016 A | 5/1999 | Ferrand et al. | |
| 5,911,222 A | 6/1999 | Lawrence et al. | |
| 5,914,264 A | 6/1999 | Korman | |
| 5,921,972 A | 7/1999 | Skow | |
| 5,926,884 A | 7/1999 | Biggie et al. | |
| 5,931,797 A | 8/1999 | Tumey et al. | |
| 6,056,730 A | 5/2000 | Greter | |
| 6,071,267 A | 6/2000 | Zamierowski | |
| 6,102,935 A | 8/2000 | Harlan et al. | |
| 6,102,936 A | 8/2000 | Augustine et al. | |
| 6,117,111 A | 9/2000 | Fleischmann | |
| D434,150 S | 11/2000 | Tumey et al. | |
| 6,142,982 A | 11/2000 | Hunt et al. | |
| 6,174,306 B1 | 1/2001 | Fleischmann | |
| 6,200,195 B1 * | 3/2001 | Furuno et al. | 450/81 |
| 6,203,563 B1 | 3/2001 | Fernandez | |
| 6,290,685 B1 | 9/2001 | Insley et al. | |

| | | | |
|---|---|---|---|
| 6,299,593 B1 | 10/2001 | Wakabayashi | |
| 6,345,623 B1 | 2/2002 | Heaton et al. | |
| 6,375,240 B1 | 4/2002 | Lindberg | |
| 6,387,065 B1 | 5/2002 | Tumey | |
| 6,398,767 B1 | 6/2002 | Fleischmann | |
| 6,420,622 B1 | 7/2002 | Johnston et al. | |
| 6,458,109 B1 | 10/2002 | Henley et al. | |
| 6,468,237 B1 | 10/2002 | Lina | |
| 6,493,568 B1 | 12/2002 | Bell et al. | |
| 6,500,112 B1 | 12/2002 | Khouri | |
| D469,175 S | 1/2003 | Hall et al. | |
| D469,176 S | 1/2003 | Hall et al. | |
| 6,551,280 B1 | 4/2003 | Knighton et al. | |
| 6,553,998 B2 | 4/2003 | Heaton et al. | |
| D475,132 S | 5/2003 | Randolph | |
| D475,134 S | 5/2003 | Randolph | |
| 6,557,704 B1 | 5/2003 | Randolph | |
| 6,592,889 B1* | 7/2003 | Stout et al. | 424/443 |
| D478,659 S | 8/2003 | Hall et al. | |
| 6,620,132 B1 | 9/2003 | Skow | |
| 6,626,891 B2 | 9/2003 | Ohmstede | |
| 6,641,527 B2 | 11/2003 | Khouri | |
| 6,641,575 B1 | 11/2003 | Lonky | |
| 6,663,610 B1 | 12/2003 | Thompson et al. | |
| 6,685,681 B2 | 2/2004 | Lockwood et al. | 604/305 |
| 6,695,823 B1 | 2/2004 | Lina et al. | |
| 6,752,794 B2 | 6/2004 | Lockwood et al. | |
| 6,755,807 B2* | 6/2004 | Risk et al. | 604/319 |
| 6,764,462 B2 | 7/2004 | Risk, Jr. et al. | 604/67 |
| 6,800,074 B2 | 10/2004 | Henley et al. | 604/319 |
| 6,824,533 B2 | 11/2004 | Risk, Jr. et al. | 604/319 |
| 6,855,135 B2 | 2/2005 | Lockwood et al. | 604/313 |
| 7,022,113 B2 | 4/2006 | Lockwood et al. | 604/313 |
| 7,198,046 B1 | 4/2007 | Argenta et al. | 128/897 |
| 7,216,651 B2 | 5/2007 | Argenta et al. | 128/897 |
| 2001/0029956 A1 | 10/2001 | Argenta et al. | |
| 2002/0082567 A1* | 6/2002 | Lockwood et al. | 604/307 |
| 2002/0115952 A1 | 8/2002 | Johnson et al. | |
| 2002/0143286 A1 | 10/2002 | Tumey | |
| 2002/0161346 A1 | 10/2002 | Lockwood et al. | |
| 2003/0050594 A1 | 3/2003 | Zamierowski | |
| 2003/0108587 A1 | 6/2003 | Orgill et al. | |
| 2004/0039415 A1 | 2/2004 | Zamierowski | |

FOREIGN PATENT DOCUMENTS

| | | |
|---|---|---|
| DE | 847475 | 6/1952 |
| DE | 2809828 | 9/1978 |
| DE | 41 11 122 A1 | 4/1993 |
| EP | 0 620 720 B1 | 3/1998 |
| EP | 0 688 189 B1 | 9/2000 |
| GB | 641061 | 8/1950 |
| GB | 1273342 | 5/1972 |
| GB | 2125296 A | 3/1984 |
| GB | 2 380 255 A * | 4/2003 |
| JP | 1005548 A2 | 1/1989 |
| WO | WO90/11795 | 10/1990 |
| WO | WO91/00718 | 1/1991 |
| WO | WO91/16030 | 10/1991 |
| WO | WO92/19313 | 11/1992 |
| WO | WO92/20299 | 11/1992 |
| WO | WO93/09736 | 5/1993 |
| WO | WO94/20041 | 9/1994 |
| WO | WO96/05873 | 2/1996 |
| WO | WO 00/32247 A2 * | 6/2000 |

OTHER PUBLICATIONS

"HiBlow Air Pump", Techno Takatsuki Co., Ltd., Osaka, Japan (1 page).
Philbeck Jr., et al., "The Clinical and Cost Effectiveness of Externally Applied Negative Presure Wound Therapy in the Treatment of Wounds in Home Healthcare Medicare Patients", Ostomy/Wound Management, Jan. 1999; 45(11):41-50.
Murphy et al., "Options in Practice: Care of An Obese Patient with a Pressure Ulcer," 2001, JWOCN, 28:171-6.
Morykwas, Michael et al., "Vacuum-Assisted Closure: A New Method for Wound Control and Treatment: Animal Studies and Basic Foundation," Annals of Plastic Surgery, Jun. 1997, vol. 38, No. 6 (pp. 553-562).
Mendez-Eastman, Susan, "Negative Pressure Wound Therapy," Plastic Surgical Nursing, Spring 1988, vol. 18, No. 1, (pp. 27-29, 33-37).
Schneider, Andrew et al., "A New and Reliable Method of Securing Skin Grafts to the Difficult Recipient Bed," Plastic and Reconstructive Surgery, Sep. 1998, vol. 102, No. 4 (pp. 1195-1198).
Rohrich, Rod J. et al., "An Algorithm for Abdominal Wall Reconstruction," Plastic and Reconstructive Surgery, Jun. 2000, vol. 105, No. 1 (pp. 202-216).
Morykwas, Michael J. et al., "Nonsurgical Modalities to Enhance Healing and Care of Soft Tissue Wounds," Journal of the Southern Orthopedic Association, Winter 1997, vol. 6, No. 4 (pp. 279-288).
Meara, John G. et al., "Vacuum-Assisted Closure in the Treatment of Degloving Injuries," Annals of Plastic Surgery, Jun. 1999, vol. 42, No. 6 (pp. 589-594).
Molnar, Joseph A. et al., "Single Stage Approach to Skin Grafting the Exposed Skull," Plastic and Reconstructive Surgery, Jan. 2000, vol. 105, No. 1 (pp. 174-177).
Joseph, Emmanuella et al., "A Prospective Randomized Trial of Vacuum-Assisted Closure Versus Standard Therapy of Chronic Nonhealing Wounds," Wounds 2000, 12(3):60-67.
Greer, Steven E. et al., "Techniques for Applying Subatmospheric Pressure Dressing to Wounds in Difficult Regions of Anatomy," JWOCN, Sep. 1999, vol. 26, No. 5 (pp. 250-253).
Obdeijn, Miryam C. et al., "Vacuum-Assisted Closure in the Treatment of Poststernotomy Mediastinitis", Ann. Thoracic Surgery, 1999, 68:2358-60.
Werner, H.P., "Complications and Risks of Suction Drainage", Z Gesamte Hyg., Feb. 1990 36(2):94-9 (Abstract—1 page).
Rosser, Charles, et al., "A New Technique to Manage Perineal Wounds," Infections in Urology, Mar./Apr. 2000 (4 pages).
V.A.C.® Recommended Guidelines for Use, Physician & Caregiver Reference Manual, KCI, San Antonio, Texas (20 pages).
MiniV.A.C.™ Vacuum Assisted Closure Summary Sheet, KCI, San Antonio, Texas (4 pages) © 2000, 2001.
The V.A.C® System, The Truth About Misuse . . . , KCI, San Antonio, Texas, Oct. 2000 (2 pages).
V.A.C.® Soft Foam, KCI, San Antonio, Texas, Aug. 2001 (4 pages).
The V.A.C. Patient and Family Handbook, KCI, San Antonio, Texas (21 pages).
Mendez Eastman, Susan, "When Wounds Won't Heal", RN, Jan. 1998 (pp. 1-8).
Argenta, Louis C. et al., "V.A.C.® Wound Closure Device Case Study #1", KCI Therapeutic Services, Inc., San Antonio, Texas, Apr. 1998 (1 page).
"V.A.C.® Wound Closure Device Case Study #6", KCI Therapeutic Services, Inc., San Antonio, Texas, Apr. 1998 (2 pages).
"The V.A.C.® Case Study #7", KCI Therapeutic Services, Inc., San Antonio, Texas, Jun. 1996 (2 pages).
"V.A.C.® Wound Closure Device Case Study #8", KCI Therapeutic Services, Inc., San Antonio, Texas, Apr. 1998 (2 pages).
"The V.A.C.® Case Study #10", Kinetic Concepts, Inc., © 1996 (2 pages).
"V.A.C.® Wound Closure Device Case Study #11", KCI Therapeutic Services, Inc., San Antonio, Texas, Apr. 1998 (2 pages).
Arturson, Gosta M., "The Pathophysiology of Severe Thermal Injury," JBCR, Mar./Apr. 1985, 6(2):129-146.
Clark, R.A.F., et al., The Molecular and Cellular Biology of Wound Repair, Chapter 1 (1988) (33 pages), Plenum Press, New York.
Mulder, G.D., et al. Clinician's Pocket Guide to Chronic Wound Repair, 1991, pp. 54-55, Wound Healing Publications, Spartanburg, SC.
Chariker, M.E. et al., "Effective Management of Incisional and Cutaneous Fistulae with Closed Suction Wound Drainage," Contemporary Surgery, Jun. 1989, pp. 59-63, vol. 34.
Jeter, K.F. et al. "Managing Draining Wounds and Fistulae: New and Established Methods," Chronic Wound Care: Health Management Publications, 1990, pp. 240-246.

"What's So Special About The Moblvac II Portable Suction System?", Aeros, (1 page).
"Care-E-Vac", Aeros, Aug. 1993 (2 pages).
"Emerson Post-Operative Suction Pumps", Emerson, Series 55. J.H. Emerson Co., Cambridge, MA, (1 page).
"Emerson Transport Suction Unit", Emerson, J.H. Emerson Co., Cambridge, MA, (1 page).
"Instavac Aspirator", Aeros, Aeros Instruments, Inc., Northbrook, IL Oct. 1988, Part No. 1504-02 7M. (1 page).
"Pleur-evac. Adult-Pediatric, Non-Metered." Code No. A-4000. Control No. F7961J (5 pages).
"TUGS (Transportable Universal Gradient Suction", Instruction Manual, Creative Medical Laboratories, Inc., Rochester, Minn. (7 pages).
"Pleur-evac", Deknatel, Div. of Howmedica, Inc. Queens Village, NY (1 page).
"Power Source Multi-Purpose Surgical Aspirator" Sparta Instrument Corp., Hayward, CA (1 page).
"Point 5 Aspirator", Wells Johnson Company, Tucson, AZ (2 pages).
"Wound-Evac ET Closed Wound Suction System", Microtek Heritage, Columbus, MS, No. 0012 (4 pages).
Fleischmann, W., Wund Forum Spezial. IHW '94. "Vakuumversiegelung zur Behandlung von Problemwunden" (with English translation: Vacuum Sealing for Treatment of Problematical Wounds) (7 pages).
Fleischmann, W., "Treatment of Bone and Soft Tissue Defects in Infected Nonunion", Acta Orthopaedica Belgica Suppl. I-1992, vol. 58 (9 pages).
Fleischmann, W., "Vakuumversiegelung zur Behandlung des Weichteilschadens bei offenen Frakturen." (English abstract, no English translation) (5 pages) Unfall Chirurg. Springer-Varlag 1993.
Valenta, A., "Using the Vacuum Dressing Alternative for Difficult Wounds", American Journal Of Nursing, Apr. 1994 (2 pages).
Letsou et al. "Stimulation of Adenylate Cyclase Activity in Cultured Endothelial Cells Subjected to Cyclic Stretch." J Cardiovascular Surgery 31. Toronto. Sep. 1990 (pp. 634-639).
Bucalo et al. "Inhibition of Cell Proliferation by Chronic Wound Fluid." Wound Repair and Regeneration. Jul.-Sep. 1993 (pp. 181-186).
Falanga, Vincent. "Growth Factors and Chronic Wounds: The Need to Understand the Microenvironment." Journal of Dermatology, vol. 19, 1992 (pp. 667-672).
Urschel et al. "The Effect of Mechanical Stress on Soft and Hard Tissue Repair; a Review." British Journal of Plastic Surgery, 1988 vol. 41 (pp. 182-186).
Gogia, Prem P. "The Biology of Wound Healing." Ostomy/Wound Management. Nov.-Dec. 1992. pp. 12-20.
Olenius et al., "Mitotic Activity in Expanded Human Skin." Plastic and Reconstructive Surgery. Feb. 1993, pp. 213-215, vol. 91, No. 2.
Rastgeldi, S., "I. Pressure Treatment of Peripheral Vascular Diseases. II. Intermittent Pressure Treatment of Peripheral Vascular Diseases.", Opuscula Medica, Suppl. XXVII, 1972 (49 pages).
Author Unknown., "Hyperemia by Suction Apparatus", Chapter VIII, pp. 74-85.
Saunders, J.W., "Negative-Pressure Device for Controlled Hypotension During Surgical Operations", The Lancet, Jun. 28, 1952, pp. 1286-1287.
Landis et al., "The Effects of Alternate Suction and Pressure on Blood Flow to the Lower Extremities," Robinette Foundation of the Hospital of the University of Pennsylvania, (pp. 925-961).
Hargens et al., "Control of Circulatory Functions in Altered Gravitational Fields" Space Physiology Laboratory, Life Science Division, NASA, Ames Research Center (4 pages).
Wolthuis et al., "Physiological Effects of Locally Applied Reduced Pressure in Man" Physiological Reviews, Jul. 1974, 54:566-595.
Viljanto et al., "Local hyperalimentation of open wounds", BR J Surg., 1976, 63:427-430.
Dillon, "Treatment of Resistant Venous Stasis Ulcers and Dermatitis with the End-Diastolic Pneumatic Compression Boot", Angiology—The Journal of Vascular Diseases, Jan. 1986, pp. 47-55.
Lundvall et al., "Transmission of externally applied negative pressure to the underlying tissue. A study on the upper arm of man", Acta Physiol Scand, 136: 403-409, accepted Jan. 28, 1989.
Klemp et al., "Subcutaneous Blood Flow in Early Male Pattern Baldness", The Journal of Investigative Dermatology, 1989, pp. 725-726.
A. Harle, "Schwachstellen herkömmlicher Drainagen", Z. Orthop., 1989, 127: 513-517.
Dunlop et al., "Vacuum drainage of groin wounds after vascular surgery: a controlled trial", Br. J. Surg., 1990, 77: 562-563.
Maddin et al., "The Biological Effects of a Pulsed Electrostatic Field with Specific Reference to Hair: Electrotrichogenesis", International Journal of Dermatology, 1990, 29: 446-450.
Nakayama et al., "A New Dressing Method for Free Skin Grafting in Hands", Ann. Plast. Surg., 1991, 26: 499-502.
Hargens et al., "Lower Body Negative Pressure to Provide Load Bearing in Space", Aviation, Space and Environmental Medicine, Oct. 1991, pp. 934-937.
"Wells Johnson Suction Tips", American Journal Of Nursing, Apr. 1994 (1 page).
"Miscellaneous Equipment" IEN Industrial Equipment News, Skokie, IL, (1 page).
Wysocki et al., "Wound Fluid from Chronic Leg Ulcers Contains Elevated Levels of Metalloproteinases MMP-2 and MMP-9." The Society for Investigative Dermatology, Inc., Jul. 1993 (pp. 64-68).
Finley, John M., M.D., "Subclavian Intravenous Catheters", Manual of Wound Dressings, pp. 124-148.
Fleck, et al., "When Negative is Positive: A Review of Negative Pressure Wound Therapy," For submission to the Mar./Apr. 2004 ECPN Wound Care Column (12 pages).
Obdeijn, Miryam C. et al., "Vacuum-Assisted Closure in the Treatment of Poststernotomy Mediastinitis," Ann. Thoracic Surgery, 1999; 68:2358-60.
ConstaVac™ Closed Wound Drainage System, Stryker Instruments (2 pages).
Serry, Cyrus, et al., "Sternal Wound Complications: Management and Results," J Thorac Cardiovasc Surg, 1980, 80:861-867.
Tang, A.T.M., et al., "Vacuum-Assisted Closure to Treat Deep Sternal Wound Infection Following Cardiac Surgery," Journal of Wound Care, May 2000, vol. 9, No. 5 (3 pages).
Argenta, Louis C. et al., "Vacuum-Assisted Closure: A New Method for Wound Control and Treatment: Clinical Experience," Annals of Plastic Surgery, Jun. 1997, vol. 38, No. 6 (15 pages).
Putney, F. Johnson, M.D., "The Use of Continuous Negative Pressure After Laryngectomy and Radical Neck Dissection," Surgery, Jul. to Dec. 1956, vol. 103 (5 pages).
Fay, Margaret F., "Drainage Systems—Their Role in Wound Healing," Aorn Journal, Sep. 1987, vol. 46, No. 3 (10 pages).
Fox, James W. et al. "The Use of Drains in Subcutaneous Surgical Procedures," The American Journal of Surgery, Nov. 1976, vol. 132 (3 pages).
Sames, C. Patrick, "Sealing of Wounds With Vacuum Drainage" (1 page).
Davis, T. P., "The Advantages of Suction Drainage in Surgical Wounds," The Medical Journal of Australia, Feb. 1, 1958 (3 pages).
Hartz, Renee S. et al., "Healing of the Perineal Wound," Arch Surg. Apr. 1980, vol. 115 (5 pages).
Morris, A. M., "A Controlled Trial of Closed Wound Suction, Drainage in Radical Mastectomy," The British Journal of Surgery, Jan. 1973 to Dec. 1973, vol. 60 (4 pages).
Berman, Arnold T., et al., "Comparison Between Intermittent (Spring-Loaded) and Continuous Closed Suction Drainage of Orthopedic Wounds: A Controlled Clinical Trial," Orthopedics, Mar. 1990 vol. 13/No. 3 (8 pages).
McFarlane, R. M., "The Use of Continuous Suction Under Skin Flaps," British Journal of Plastic Surgery, 1958-59, vol. XI (12 pages).
Sutton, Warren T. et al., "Suction for Postoperative Wounds," Archives of Surgery, Jan. through Jun. 1961, vol. 82 (8 pages).
Lesser, Arthur J., "The Place of Wound Drainage in Surgery with Description of a New Drain," Archives of Surgery, Dec. 1960, vol. 81, No. 6 (9 pages).
Sheppard, M. D. et al., "Sealed Drainage of Wounds," The Lancet, Jan.-Jun. 1952, vol. One (5 pages).

Ramirez, Oscar M. et al., "Optimal Wound Healing Under Op-Site Dressing," Plastic and Reconstructive Surgery, Mar. 1984, vol. 73, No. 3 (3 pages).

Silvis, Richard S. et al., "The Use of Continuous Suction Negative Pressure Instead of Pressure Dressing," Annals of Surgery, Jul.-Dec. 1955, vol. 142 (7 pages).

Giovannini, Uberto M., et al., "Interest of Negative Pressure Therapy in the Treatment of Postoperative Sepsis in Cardiovascular Surgery," Wounds, 2001, Health Management Publications, 13(2):82-87. (7 pages).

Kostiuchenok, B. M., et al., "The Vacuum Effect in the Surgical Treatment of Purulent Wounds," Russian Journal, Vestnik Khirurgii, Sep. 1986 (pp. 18-21).

Davydov, Yu A., et al., "Vacuum Therapy in the Treatment of Purulent Lactation Mastitis," Russian Journal, Vestnik Khirurgii, Sep. 1986 (pp. 66-70).

Usupov, Y. N. et al., "Active Wound Drainage," Russian Journal, Vestnik Khirurgii, Apr. 1987 (pp. 42-45).

Davydov, Yu A., et al., "The Bacteriological and Cytological Assessment of Vacuum Therapy of Purulent Wounds," Russian Journal, Vestnik Khirurgii, Oct. 1988, (pp. 48-52).

Davydov, Yu A., et al., "Concepts for Clinical Biological Management of the Wound Process in the Treatment of Purulent Wounds Using Vacuum Therapy," Russian Journal, Vestnik Khirurgii, Feb. 1991 (pp. 132-135).

Healy DA., et al., "Prophylactic closed suction drainage of femoral wounds in patients undergoing vascular reconstruction," Journal of Vascular Surgery, Aug. 1989, 10(2):166-8 (Abstract-1 page).

Davydov IA., et al., "Vacuum therapy of actue supportive diseases of soft tissues and suppurative wounds," Vestnik Khirurgii Imeni i—i—Grekova. Sep. 1988, 141(9):43-6 (Abstract-1 page).

Tadych K., et al., "Postmastectomy seromas and wound drainage," Surgery, Gynecology & Obstetrics, Dec. 1876, 165(6):483-7 (Abstract-1 page).

Iusupov IN, et al., "Active drainage of a wound," Vestnik Khirurgii Imeni i—i—Grekova. Apr. 1987, 138(4):42-6 (Abstract-1 page).

Hendrich V. et al., "Suction-drainage in the treatment of chronic osteomyelitis," Unfallchirurgie. Apr. 1986, 12(2):101-3 (Abstract-1 page).

Harle A., "Postoperative wound suction drainage and its effect on wound healing," Zeitschrift fur Orthopadie und Ihre Grenzgebiete. May-Jun. 1985, 123(3):395-402 (Abstract-1 page).

Smith SR., et al., "Surgical drainage," British Journal of Hospital Medicine, Jun. 1985, 33(6):308, 311, 314-15 (Abstract-1 page).

Lokhvitski SV. Bil'Kevich AA., "[Treatment of carbuncles]," Vestnik Khirurgii Imeni i—i—Grekova, Jan. 1984, 132(1):71-4 (Abstract-1 page).

Harle A., "Weakness of conventional drainage systems," Zeitschrift fur Orthopadie und Ihre Grenzgebiete, Jul.-Aug. 1989, 127(4):513-7 (Abstract-1 page).

Durandy Y., et al., "Mediastinal infection after cardiac operation. A simple closed technique." Journal of Thoracic & Cardiovascular Surgery, Feb. 1989, 97(2):282-5 (Abstract-1 page).

Healy DA., et al., "Prophylactic closed suction drainage of femoral wounds in patients undergoing vascular reconstruction." Journal of Vascular Surgery, Aug. 1989, 10(2):166-8 (Abstract-1 page).

Gerngross H., et al., "Gravity drainage versus suction drainage: an experimental and clinical study." Unfallchirurg. Jan. 1989, 92(1):37-42 (Abstract-1 page).

Draca, P., et al., "Extraperitoneal transabdominal vacuum drainage of the parametrial cavity and suprapubic drainage of the urinary bladder after radical hysterectomy." Jugoslavenska Ginekologija i Perinatologija, May-Aug. 1989, 29(3-4):129-32 (Abstract-1 page).

Willett KM., et al., "The effect of suction drains after total hip replacement." Journal of Bone & Joint Surgery, Aug. 1988, British vol. 70 (4):607-10 (Abstract-1 page).

Tittel K., et al., "VariDyne—new standards in postoperative wound drainage." Unfallchirurgie. Apr. 1988, 14(2):104-7 (Abstract-1 page).

Davydov IA., et al., "Vacuum therapy of actute suppurative diseases of soft tissues and suppurative wounds." Vestnik Khirurgii Imeni i—i—Grekova., Sep. 1988, 141(9):43-6 (Abstract-1 page).

Tadych K., et al., "Postmastectomy seromas and wound drainage." Surgery, Gynecology & Obstetrics, Dec. 1987, 165(6):483-7 (Abstract—1 page).

Moss AL., "The DIY mini suction drain." British Journal of Plastic Surgery, Sep. 1987, 40(5):542-3 (Abstract-1 page).

Iusupov IN, et al., "Active drainage of a wound." Vestnik Khirurgii Imeni i—i—Grekova. Apr. 1987, 138(4):42-6 (Abstract-1 page).

Orr JW., et al., "Closed suction pelvic drainage after radical pelvic surgical procedures." American Journal of Obstetrics & Gynecology, Oct. 1986, 155(4):867-71 (Abstract-1 page).

Svedman P., et al., "A dressing system providing fluid supply and suction drainage used for continuous or intermittent irrigation." Annals of Plastic Surgery, Aug. 1986, 17(2):125-33 (Abstract-1 page).

Nasser NA., "The use of the Mini-Flap wound suction drain in maxillofacial surgery." Annals of the Royal College of Surgeons of England., May 1986, 68(3):151-3 (Abstract-1 page).

Hendrich V., et al., "Suction-drainage in the treatment of chronic osteomyelitis." Unfallchirurgie, Apr. 1986, 12(2):101-3 (Abstract-1 page).

Diament MJ., et al., "Percutaneous aspiration and catheter drainage of abscesses." Journal of Pediatrics, Feb. 1986, 108(2):204-8 (Abstract-1 page).

Chinn SD, et al., "Closed wound suction drainage." Journal of Foot Surgery, Jan.-Feb. 1985, 24(1):76-81 (Abstract-1 page).

Harle A., "Postoperative wound suction drainage and its effect on wound healing." Zeitschrift fur Orthopadie and Ihre Grenzgebiete, May-Jun. 1985, 123(3):395-402 (Abstract-1 page).

Pruett TL., et al., Percutaneous aspiration and drainage for suspected abdominal infection. Surgery, Oct. 1984, 96(4):731-7 (Abstract-1 page).

Smith SR., et al., "Surgical drainage." British Journal of Hospital Medicine, Jun. 1985, 33(6):308, 311, 314-15 (Abstract-1 page).

Kawashima M., et al., "A new instrument for closed irrigation-suction treatment." Nippon Seikeigeka Gakkai Zasshi—Journal of the Japanese Orthopedic Association, Jun. 1983, 57(6):643-50, (Abstract-1 page).

Vergeret J., et al., "Endocavitary drainage (Monaldi's technic) in the treatment of pulmonary abscess." Revue Francaise des Maladies Respiratoires, 1983, 11(3):201-7 (Abstract-1 page).

Vatanasapt V., et al., "Red rubber bulb, cheap and effective vacuum drainage." Journal of the Medical Association of Thailand, Apr. 1989, 72(4):193-7 (Abstract-1 page).

Rudberg C., et al., "How does the increasing filling of the vacuum source diminish the suction in modern portable drainage systems?" Acta Chirurgica Scandinavica, Jan. 1988, 154(1):1-8 (Abstract-1 page).

Cooper AJ., "Preliminary experience with a vacuum constriction device (VCD) as a treatment for impotence." Journal of Psychosomatic Research, 1987, 31(3):413-8 (Abstract-1 page).

Hedges JR., et al., "Evaluation of venous distension device: potential aid for intravenous cannulation." Annals of Emergency Medicine, May 1986, 15(5):540-3 (Abstract-1 page).

Ramirez OM., et al., "Optimal wound healing under Op-Site dressing." Plastic & Reconstructive Surgery, Mar. 1984, 73(3):474-5 (Abstract-1 page).

Hollender L.F., et al., "Suction drainage in general and digestive surgery. Apropos of the use of Reliavac material." Journal de Chirurgie, Aug.-Sep. 1984, 121(8-9):539-40 (Abstract-1 page).

Nakayama Y, et al., "A new dressing method for free skin grafting in hands." Ann Plast Surg May 1991;26(5):499-502. (Abstract-1 page).

Fay MF., "Drainage systems. Their role in wound healing." AORN J Sep. 1987;46(3):442-55. (Abstract-1 page).

Durandy Y, et al., "Mediastinal infection after cardiac operation. A simple closed technique." J Thorac Cardiovasc Surg, Feb. 1989, 97(2):282-5. (Abstract-1 page).

Berger DL., "Use of drains in foot surgery." J Foot Surg., May-Jun. 1988; 27(3):245-7. (Abstract-1 page).

Insupov Iun, et al., "Active drainage of a wound." Vestn Khir Im I I Grek, Apr. 1987, 138(4):42-6. (Abstract-1 page).

Fox JW 4TH., et al., "The use of drains in subcutaneous surgical procedures." Am J Surg., Nov. 1976, 132(5):673-4. (Abstract-1 page).

Bourke JB, et al., "A comparison between suction and corrugated drainage after simple mastectomy: a report of a controlled trial." Br J Surg., Jun. 1976, 631(1):67-9. (Abstract-1 page).

Chinn SD, et al., "Closed wound suction drainage." J Foot Surg., Jan.-Feb. 1985, 24(1):76-81. (Abstract-1 page).

Guharay BN, et al., "The pacemaker-twiddler's syndrome: another disadvantage of abdominal implantation of pulse generators." Br J Surg., Sep. 1977, 64(9):655-60. (Abstract-1 page).

Elliot MS, et al., "Management of the perineal wound with constant irrigation and suction after abdominoperineal excision for cancer of the rectum. A new suction/irrigation drain." S Afr Med J., Nov. 10, 1979, 56(20):796-98. (Abstract-1 page).

Brummelkamp WH, et al. "Primary closure of the perineum and vacuum drainage after abdominoperineal excision.", Acta Chir Belg., Sep.-Oct. 1983, 83(5)358-64 (Abstract—1 page).

Garcia-Rinaldi R., et al., "Improving the Efficiency of Wound Drainage Catheters.", Am J Surg,, Sep. 1975, 130(3):372-3 (Abstract—1 page).

McCormack T.T., et al., "Abdominal drainage following cholecystectomy: high, low, or no suction?", Ann R Coll Surg., England, Sep. 1983, 65(5):326-8 (Abstract—1 page).

Saha SK, et al., "A Study of Perineal Wound Healing After Abdominoperineal Resection.", Br J Surg., Jul. 1976, 63(7):555-8 (Abstract—1 page).

Azad, S. et al., "Topical Negative Pressure May Help Chronic Wound Healing", BMJ May 4, 2002; 324:1100 (2 pages).

Author Unknown, "Three Techniques to Save the Lives of Children with Burns, to Close Wounds and Restore Walking Ability.", British Association of Plastic Surgeons, Press Release—Dec. 1996 (3 pages).

Chariker-Jeter® Wound Drainage Kit, Blue Medical, La Costa, California (1 page).

Wooding-Scott® Drainage/Irrigation Kit, Blue Sky Medical, La Costa, California (1 page).

The V.A.C. Vacuum Assisted Closure, The V.A.C. System, KCI, San Antonio, Texas (4 pages).

V.A.C.® Operations Summary, May 2001, KCI, San Antonio, Texas (2 pages).

Excerpts from Articles Published on the V.A.C.® Device, 2001, KCI, San Antonio, Texas (1 page).

Argenta, Louis C. et al., "V.A.C.® Wound Closure Device Case Study #1.", KCI Therapeutic Services, Inc., San Antonio, Texas Apr. 1998 (1 page).

Argenta, Louis C. et al. "The V.A.C.® Case Study #2", 1995 Kinetic Concepts, Inc. (1 page).

Argenta, Louis C. et al., "V.A.C.® Wound Closure Device Case Study #3", KCI Therapeutic Services, Inc., San Antonio, Texas, Apr. 1998 (1 page).

Argenta, Louis C. et al., "The V.A.C.® Case Study #4", 1995 Kinetic Concepts, Inc. (1 page).

Argenta, Louis C. et al., "V.A.C.® Wound Closure Device Case Study #5", KCI Therapeutic Services, Inc., San Antonio, Texas, Apr. 1998 (1 page).

Harkiss, K. J., "Surgical Dressings and Wound Healing", 1971 Bradford University Press and Crosby Lockwood & Son Ltd., (13 pages).

* cited by examiner

CLOSED WOUND DRAINAGE SYSTEM

CROSS-REFERENCE TO RELATED APPLICATIONS

This application is a continuation-in-part of and claims the effective filing date of application Ser. No. 10/243,004 filed Sep. 13, 2002 now U.S. Pat. No. 6,979,324 and entitled "Closed Wound Dressing System."

This application also claims the effective filing date of U.S. Provisional Application Ser. No. 60/481,165 filed on Jul. 31, 2003 and entitled "Wound Exudates Collection Bag System" and U.S. Provisional Application Ser. No. 60/481,977 filed on Jan. 30, 2004 and entitled "Wound Drain Dressing Patch."

The disclosures of the aforementioned provisional applications and regular application is incorporated by reference in their entirety herein.

FIELD OF THE INVENTION

The present invention relates to systems for treating wounds by the application of negative pressure, and to devices for use in such systems.

SUMMARY OF THE INVENTION

One embodiment of the present invention includes a closed wound dressing system comprising a layer of gel for application to the upper surface of a wound area and forming a cavity open to the wound adjacent the lower surface of said gel layer, the gel layer being sized to extend beyond the upper surface of the wound area for attachment to healthy skin outside the wound area, the lower surface of the layer of gel adhering to the skin around the wound. A tube extends into the gel cavity, which contains a porous packing. A vacuum pump is attached to the proximal end of the tube to apply a negative pressure to the tube and thus to the cavity formed by the gel. In a preferred embodiment, a porous material is attached to the lower surface of the gel and extends across the opening to the cavity below the distal end of the tube so that material drawn from a wound into the tube passes through the porous material, and a container is connected to a proximal end portion of the tube to accept material drawn into the tube from a wound.

Another embodiment of the present invention provides a portable, flexible and disposable single-use wound exudates collection bag ("WECB") system. The WECB is used to collect exudates, fluids and other debris withdrawn from a wound dressing used to treat a wound with negative pressure. The collection bag preferably has associated tubes which attach to a wound dressing and a drain/suction unit. The drain/suction unit creates negative pressure inside the WECB to pull exudates through a drainage tube which is attached at one end to the wound dressing, and at the other end to the WECB. As the WECB is filled with exudate, the pressure increases. When the pressure reaches a preset value, the pump is turned off to prevent overfilling of the WECB. The WECB also preferably includes gelling material that transforms the exudate into a thick non-viscous mass which will not leak out of the WECB.

A further embodiment of the invention provides a flexible wound dressing patch system ("WDP") that can be applied to a wound. The WDP provides a flexible single-piece wound dressing patch with a gel-like consistency that allows it to conform to the surface contours of a patient's body. The patch has an integrated wound drain that is held in place in the wound by the patch and removes exudates from a wound via a vacuum tube that extends through the wall of the patch. The side of the patch facing away from the surface of the patient's body is covered with a layer of bandage material to facilitate handling and to protect the patch. The WDP may also have an integrated dressing cover that extends past the peripheral edge of the patch and secures to the skin surface of the patient to protect the patch from environmental factors. The dressing cover, the patch, and the wound drain can optionally be made as a single unit to facilitate rapid attachment of the WDP to the wound of a patient in a single step.

DETAILED DESCRIPTION OF THE PREFERRED EMBODIMENTS

Figure 1A:
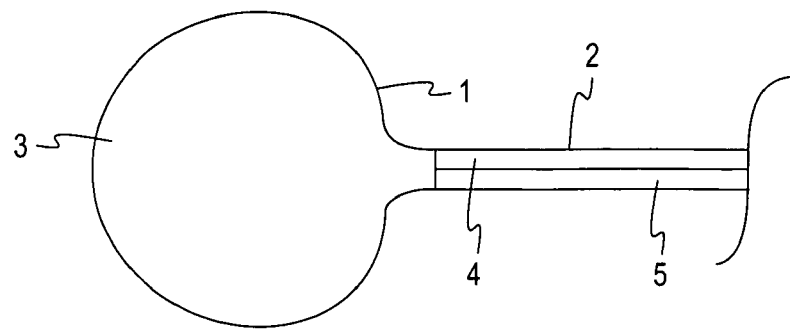
FIG. 1a is a top view of a preferred embodiment of the pouch with a multiple lumen section of tubing inserted in the pouch.

The negative pressure wound treatment system of this invention is designed to eliminate much of the discomfort and pain of having a dressing installed in a wound. Turning first to FIGS. 1-6 of the drawings, one embodiment of a wound dressing for use in a negative-pressure treatment system comprises five main components, namely, a pouch 1, tubing 2, a drain/suction unit 14, a sealant 12, and a protective cover 13.

In FIG. 1a, a top view of a preferred embodiment of the pouch 1 is shown. The upper surface 3 of the pouch 1 is intended to be made with a nonporous material to prevent any leakage of exudates from the wound, through the pouch 1, to the outside of the dressing where it may cause contamination of others. The upper surface 3 of the pouch 1 can be made with any suitable material so long as it retains its flexibility and prevents leakage of exudates through the upper surface 3. For ease of illustration, the shape of the pouch 1 is shown as having a generally circular structure. Those skilled in the art will recognize that since the pouch 1 is intended to be a flexible and malleable device which is conformed to the shape of a patient's wound, the exact shape of the pouch 1 is not critical and may vary in both size and shape.

Figure 1B:
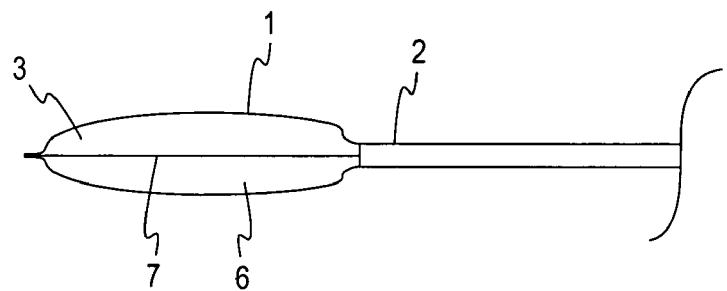
FIG. 1b is a side view of a preferred embodiment of the pouch with a section of tubing inserted into the pouch.

FIG. 1b illustrates a side view of the preferred embodiment of FIG. 1a. In this figure, the pouch 1 is shown with a section of tubing 2 inserted into it. Also shown in this figure is the lower surface 6 of the pouch 1. As noted above, the upper surface 3 is intended to be nonporous to prevent exudates from leaking out of the pouch 1. However, the lower surface 6 of the pouch 1 is intended to be porous to allow exudates and other material from the wound cavity to be absorbed into the pouch 1 from which it can be later removed and discarded. The upper surface 3 and the lower surface 6 are joined at seam 7 to form a pouch structure with an internal chamber which holds filler.

Figure 1C:
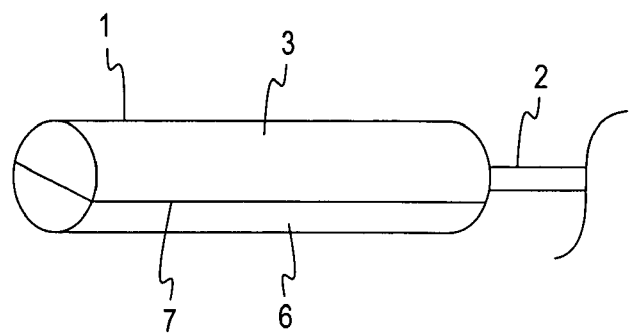
FIG. 1c is a perspective view of an alternative preferred embodiment of the pouch showing a generally tubular shaped pouch structure.

A perspective view of an alternative preferred embodiment is shown in FIG. 1c. In this embodiment, the pouch 1 is shown as having a generally tubular shaped pouch structure. This figure is intended to illustrate the fact that the actual shape of the pouch 1 is only important in that it should be convenient to insert into a wound cavity. Therefore, the pouch 1 may have any convenient shape or size, so long as it is compatible with the shape or size of a particular wound. This figure also illustrates a pouch 1 with an upper surface 3 and a lower surface 6. Those skilled in the art will recognize that in the event a pouch 1 is to be placed entirely inside a wound cavity, is also possible to provide a pouch 1 in which the entire outer surface is porous and there is no upper surface 3.

The outer surface of the pouch 1 is made from a soft flexible porous material permeable to fluids and exudates. The outer surface of the pouch 1 contains numerous small perforations or pores which allow exudates to enter the pouch and which allow suction from the drain/suction device to act on the exudates. Because it is soft and pliable, the pouch 1 can be installed by medical personnel to snugly fit within a wound cavity. When placed inside the wound cavity, fluids and exudates in the wound pass through the outer surface of the pouch 1 and are absorbed by porous material inside the pouch. Later, the exudates are drawn out through the tubing for disposal. The pouch 1 may be formed in any suitable shape or size. For example, pouches can be flat, spherical, tubular, irregular, etc. The only requirement as to shape and size is that the pouch 1 is suitable to treat a particular size and shape of wound.

Another optional feature of the pouch 1 is that it can be formed such that it provides active treatment of bacterial agents. For example, the pouch can be used as a means to deliver medications, such as antibiotics, which are pumped into the pouch via the tubing. The pouch normally contains beads or fillers. They can be loose, or secured around the tubing inserted in the pouch. The filler can be any antimicrobial material or equivalent. If the filler in the pouch 1 is impregnated with antibiotics or other medications, they can leak into the wound area to assist healing in addition to destroying infectious material encountered inside the pouch. The shape of the beads/filler allows the pouch to be conformed to the shape of the wound. Further, at least some of the beads may be fabricated from material with known antibacterial properties, such as silver.

The pouch has a number of advantages over conventional dressings. It conforms to tissue contours, thereby avoiding the situation where an area of a wound is left to dry out or accumulate fluids. It is a self-contained single-use device which is preferably made in inexpensive disposable form. It can be used in conjunction with other commercially available dressing materials, or can be adapted to work in combination with other commercially available dressings. The material used for the pouch 1 is biocompatible. It may contain active medications for drug delivery to wound site, it may contain conductive material to allow measurement of electrical parameters, it may deliver continuous proposed electromagnetic field therapy, and/or it may be used to provide low current electrical stimulation in conjunction with low temperature heat. It provides self-adherence when used with a sealant agent and a protective cover which may also function as a wound margin skin protectant. Because it fills the wound cavity, the pouch prevents pooling of exudates which would otherwise prevent or slow down the healing process. It is bidirectional in the sense that it provides for the drainage and removal of infectious material and fluids, as well as the delivery of wound therapy in the form of medications, electrical stimulus, etc. It can be used for continuous irrigation of fluids/gases, and other microbial contaminants as well as gentle removal of debris.

The pouch has the ability to treat not only deep cavity wounds, which surface treatment devices cannot reach, but also to treat shallow surface wounds. It not only provides the ability to actively drain a wound, but it also is designed to actively deliver antibacterial agents. Likewise, it can even be constructed of materials that have natural antibacterial properties. Due to the soft, malleable properties of the pouch, it can be easily and snugly fit within wounds having a variety of shapes and conform to the shape of the wound so the entire wound cavity is filled.

The tubing 2 can be as simple as a single lumen device which only provides suction. Alternatively, the tubing may be a multi-lumen device which uses one lumen to apply negative pressure to the wound area, and a secondary lumen as a pathway to supply medications and/or antibacterial agents to the pouch for use in the wound healing process. Of course, multiple lumens may also be used for suction.

The tubing 2 is preferably a single or dual line flexible tube which is fabricated from PVC or silicone based material. However, those skilled in the art will recognize that any suitable material may be used to fabricate the tubing, and will also recognize that the number of tubes chosen can vary, so long as they achieve the goals of the invention. For example, one lumen may be used to apply negative pressure, and another lumen may be used to supply antibiotics, to irrigate a wound, or even to provide gases (e.g., oxygen) which may assist in healing the wound. In addition, a third lumen may be used to provide a path for an electrical line to provide electrical stimulation to the wound.

Figure 3:
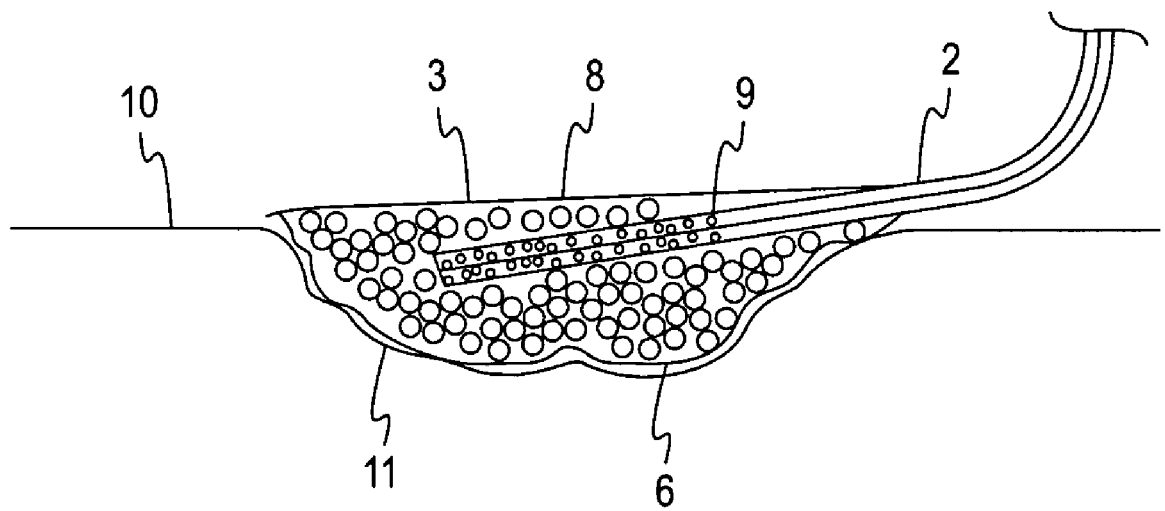
FIG. 3 is a side cutaway view of a preferred embodiment of the pouch which illustrates the pouch 1 inserted within a wound cavity.
Figure 4:
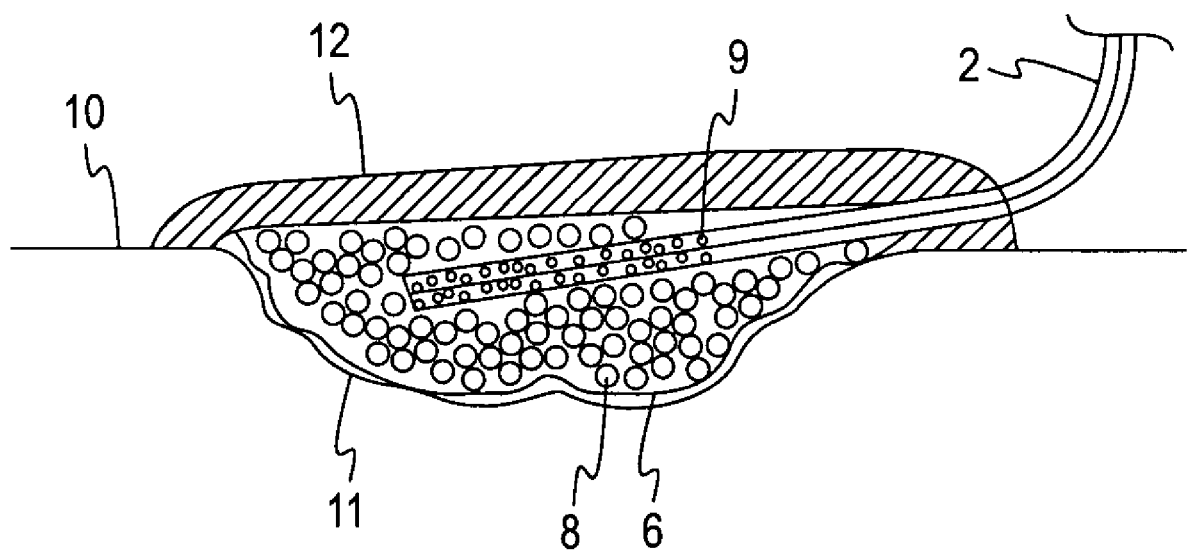
FIG. 4 is a side cutaway view of a preferred embodiment of the pouch secured inside the wound cavity by flexible get, and with tubing extending through the flexible gel.
Figure 5:
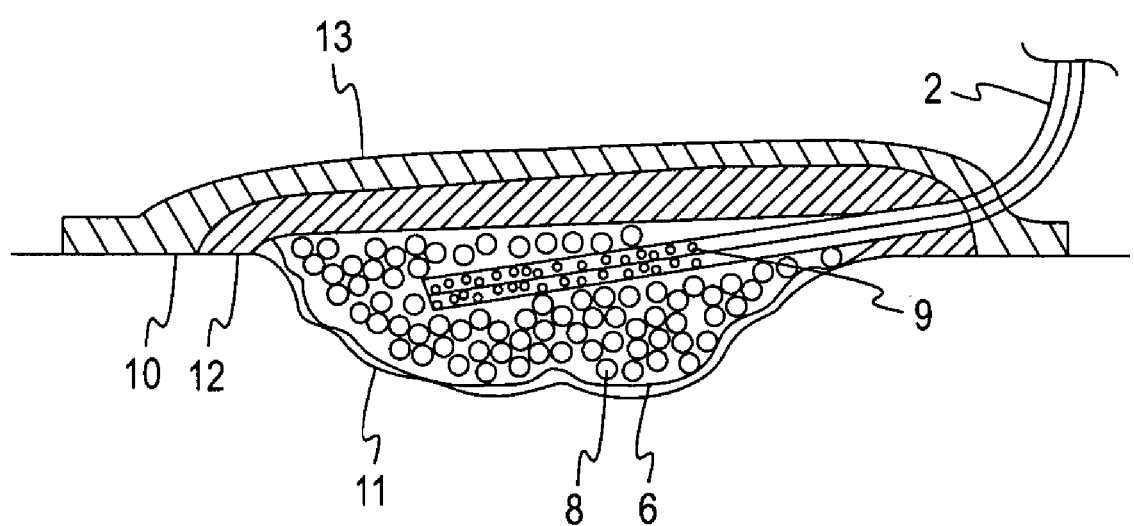
FIG. 5 is a side cutaway view of a preferred embodiment of the pouch secured inside the wound cavity by flexible gel, and with an external drape covering the gel and the wound area.

In FIGS. 3-5, the tubing 2 is shown with its distal end inserted into the pouch 1. The proximal end (shown below in regard to FIG. 6) of the tubing 2 is attached to the drain/suction unit (also shown in regard to FIG. 6). The purpose of the tubing 2 is to provide negative pressure to withdraw exudates, debris, dead cells, etc., through the tubing 2 for disposal. The tubing 2 is also intended to be sufficiently flexible such that the portion inside the pouch 1 can be easily bent when the pouch 1 is being folded or shaped to conform to the shape of a wound cavity. Likewise, the portion of the tubing 2 which is outside of the pouch 1 needs to be flexible to allow it to be manipulated to suit a particular wound and a particular patient. In the preferred embodiment, the tubing 2 is fabricated from PVC or silicone tubing similar to that used for commercially available catheter tubes. However, any material can be used to fabricate the tubing 2 so long as it is suitable for the intended purposes of the wound treatment system.

While it is possible to apply negative pressure to the wound through a single opening in the distal end of the tubing 2 (i.e., the end of the tube which is inside pouch), this approach may result in excessive force being applied to a small, localized area of the wound. Thus, a series of small perforations may be formed in the distal portion of the tubing to disperse the negative pressure and prevent it from becoming too localized. The perforations may be made in approximately the last inch of the tubing. In addition, the perforated section of the tubing is placed inside the pouch, and the perforations extend longitudinally along the tubing wall. The number of perforations and their location in regard to one another is not critical and can vary. The only requirement is that they are large enough and are sufficient enough in number to facilitate fluid flow, and are sufficiently distributed in location to avoid localized negative pressure.

More than one lumen can be used by the tubing 2 as illustrated by the multiple lumen section of tubing 2 inserted in the pouch 1. In this figure, a primary lumen 4 and a secondary lumen 5 are shown as part of the tubing 2. While the invention can work satisfactorily with a single lumen which is used to provide negative pressure, the preferred embodiment envisions multiple lumens. For example, primary lumen 4 provides negative pressure to withdraw exudates from the wound cavity, and through the pouch 1, for external disposal. In addition, secondary lumen 5 is available to perform other functions, such as delivery of medications to the pouch 1 and wound area, and delivery of gases to the pouch 1 and wound area. It also provides a path for insertion of other devices, such as electrical conductors which are used to provide low-level electrical stimulus or heat for treatment of a wound area, or other measurement or treatment devices. Of course, more than two lumens can be used depending on the nature of treatment.

Figure 6:
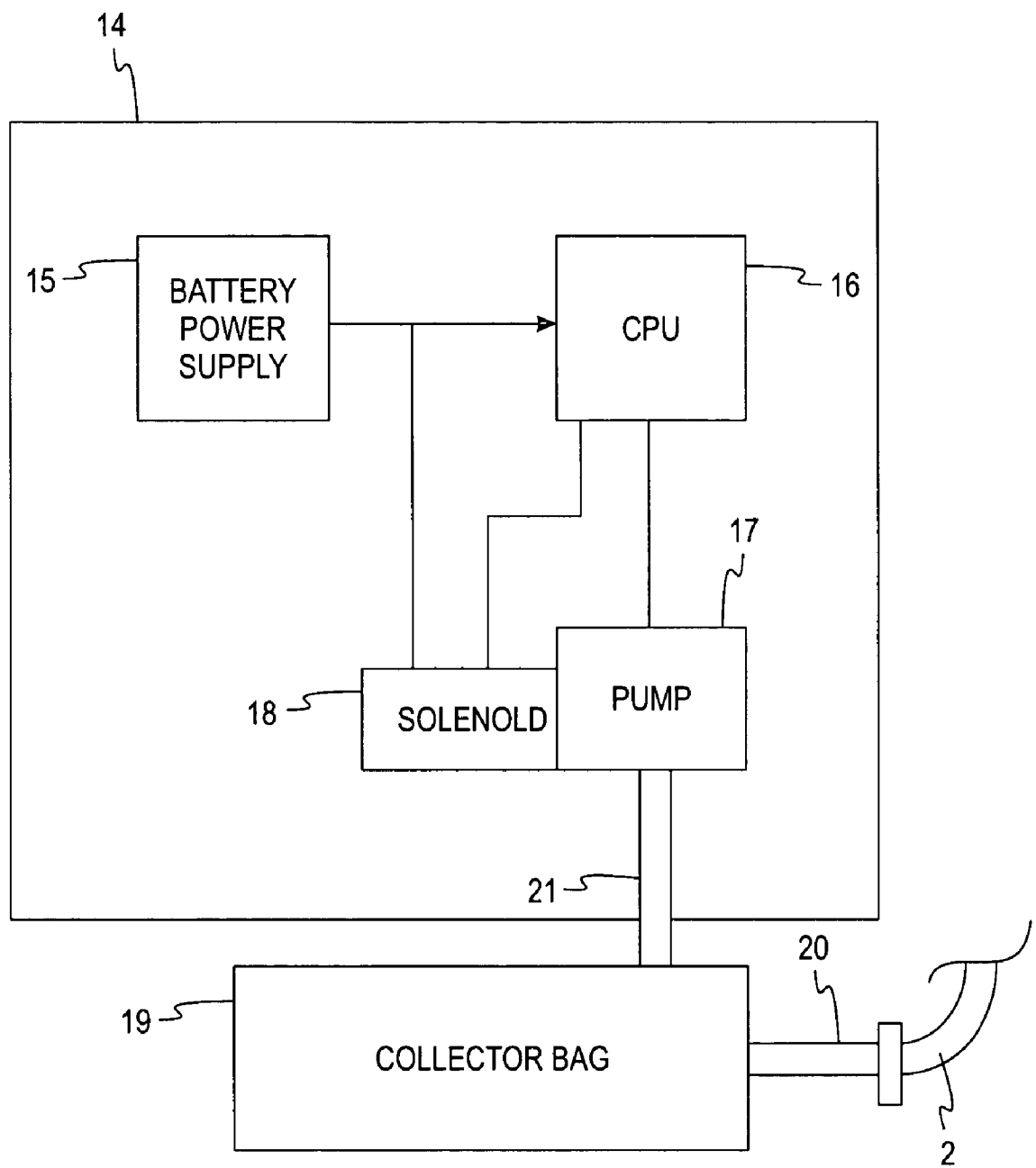
FIG. 6 is a block diagram illustrating the components of the drain/suction unit. Also shown is a section of tubing attached to the drain/suction unit.

As shown in FIG. 6, the drain/suction unit 14 includes a portable, lightweight, battery-operated, suction pump 17 which attaches to the proximal end of at least one lumen of the tubing 2. Of course, other lumens may be attached to other items, such as antibiotic drip devices, electrical devices, etc. The drain/suction unit 14 is designed such that it can be easily carried by a shoulder attachment or by attachment to the belt of the patient. In addition to the vacuum pump 17, the drain/suction unit 14 also preferably includes a reservoir 19, a battery power supply 15, and control switches 18 for turning the drain/suction unit on or off. In addition, the reservoir component 19 may have a sensor alarm to notify the patient or the medical care provider when the reservoir is almost filled. If the device is made to be portable, the patient will have the freedom to move about rather than being confined to a fixed location. A CPU 16 controls the various functions of the device and allows the patient or medical care provider to turn on and off various functions such as the application of negative pressure or the injection of medication.

The sealant 12 (see FIG. 4) seals the wound area such that contaminants cannot enter the wound area from the outside and also to prevent exudates from leaking out of the wound dressing where they may create an infection hazard to others. In a preferred embodiment the sealant 12 is a flexible gel which is applied over the top of the pouch 1 after it is placed inside the wound. The gel prevents leakage in either direction (e.g., leakage is intended to mean not only exudate leakage from the wound, but also air leakage from outside the dressing). By sealing the dressing with the gel, the environment surrounding the wound becomes more stable. In particular, both moisture and temperature will be more stable, which in turn facilitates the healing process. In addition, another significant advantage of the gel is that it is flexible and allows the patient to move about without breaking the seal between the patient's skin and the gel.

The protective cover 13 (see FIG. 5) is placed over the gel and serves several purposes. Its primary function is to protect the sealant 12 from dirt. In addition, it also helps to ensure that the sealant 12 remains in contact in and around the pouch and the wound area. It helps reduce the possibility of friction or shear when the patient is mobile. And finally, it is used for cosmetic reasons to cover the wound area.

The closed wound dressing system of FIGS. 1-6 allows a medical care provider to pack a wound with a dressing which, due to its soft and flexible nature, can be conformed to the shape of the wound and to pack the wound with a minimum amount of pain or discomfort to the patient. Because it conforms to the shape of the wound, the medical care provider does not have to spend time adjusting the size of the dressing to fit a particular shape wound which results in faster application of the dressing. Once the dressing is inserted into the wound, it provides a vehicle for delivering medications, such as antibiotics, to the wound area without having to open the dressing. The pouch is structured such that it can simultaneously deliver medications, actively combat bacteria with components fabricated from antibacterial materials, and drain a wound to facilitate rapid healing. In addition, the use of a flexible gel seals the wound area and allows a patient to engage in activities without restriction during the healing process. In the preferred embodiment, the flexible gel sealing material is a hydro-colloid, a silicone, or a lyogel, such as a hydrogel, which are all easily deformable.

Figure 2:
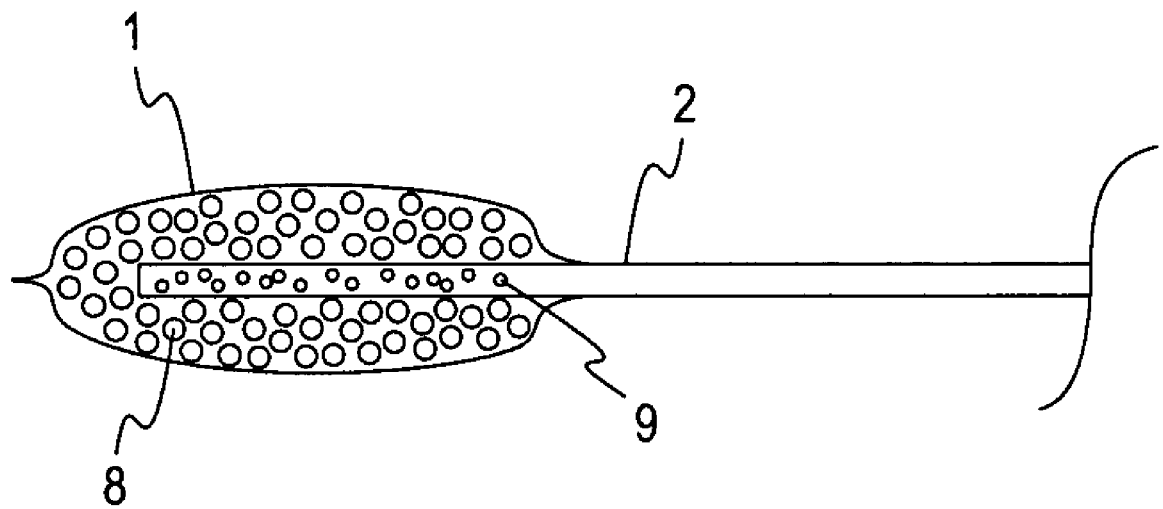
FIG. 2 is a side cutaway view of a preferred embodiment of the pouch which illustrates the pouch with a perforated section of tubing inserted inside, and beads which are used as pouch filler.

FIG. 2 is a side cutaway view of one embodiment of the pouch 1 having the distal end of the tubing 2 inserted inside the pouch 1. A series of perforations 9 arranged along the distal end of the tubing 2 allow negative pressure to be applied by the tubing 2 across a wide area of the tubing 2 which is inserted into the pouch 1. By using the perforations 9, the negative pressure is distributed over a wider area and results in a reduced chance that pressure will be applied to a small local area. As a result, exudates are pulled from a wider area of the interior of the pouch, rather than from a small area at the distal end of the tubing 2. To ensure that the negative pressure is distributed through perforations 9, the distal end of the tubing 2 is sealed.

Also shown in this figure are beads 8 which are used as a pouch filler. Because of the shape of the beads 8, they allow the shape of the pouch 1 to be more easily manipulated for insertion into a particular shaped wound cavity. In addition, they also allow exudates and other undesirable materials to move through the interior of the pouch 1 without becoming snagged inside the pouch.

The filler in the pouch 1 can be made from a variety of materials. For example, the beads 8 can be fabricated from silver which has known antimicrobial characteristics. Alternatively, they can be made from a variety of other materials which may be actively antimicrobial, or neutral, such as hydro foam, etc. In a multi-lumen embodiment, such as that shown in regard to FIG. 1a, the primary lumen 4 may be extracting exudates under negative pressure while a secondary lumen 5 may be used to inject medications, etc. into the internal cavity of the pouch 1.

FIGS. 3-5 together illustrate how the pouch 1 is installed in a wound cavity 11. The first step is illustrated in FIG. 3 which shows the pouch 1 installed within the wound cavity 11. The next step is the installation of the gel 12 which seals the wound. This step is illustrated in FIG. 4. After the gel 12 is installed, the next step is to install a cover 13 over the gel 12. This step is illustrated in FIG. 5. The cover protects the gel 12 from damage, and in addition, provides a cosmetic cover.

In regard to FIG. 3, a side cutaway view of a preferred embodiment of the pouch 1 is shown which illustrates the pouch 1 inserted into a wound cavity 11. The healthy section of the patient's skin surface 10 is also illustrated. This figure illustrates that since the pouch 1 is flexible and can be conformed to the shape of a wound 11, the entire area of the wound 11 cavity can be properly treated by the system. Also illustrated in this figure is the upper surface 3 which prevents exudates from leaking out of the pouch 1, which results in their being held in the pouch 1 until they are eventually pulled through the perforations 9 and withdrawn from the pouch 1 under negative pressure.

In FIG. 4, a side cutaway view of the preferred embodiment of FIG. 3 is shown. In this figure, the pouch 1 is secured inside the wound cavity 11 by flexible gel 12. When the flexible gel 12 is applied, it is in a viscous state which allows it to cover the pouch area from sections of healthy skin 10, and in addition, it can also seal the tubing 2 which extends through the flexible gel 12. The gel 12 preferably has flexibility to prevent it from detaching from the skin 10 if the patient is mobile. In addition, it is preferably easily deformable prior to being set to allow it to cover a particular size pouch 1 and wound 11. It should prevent contaminants from entering the wound cavity 11 and also prevent exudates from escaping the wound cavity 11 and dressing. A variety of commercially available gels can be used, such as hydro-colloids, silicones, or a lyogel, such as a hydrogel.

FIG. 5 shows a side cutaway view of a preferred embodiment of the pouch 1 which is secured inside the wound cavity 11 by flexible gel 12, and then by an external drape 13 which covers the gel 12 and the wound area. The external drape 13 is applied in the same manner that an external drape is typically applied to a wound. The external drape 13 acts as a protective cover which performs several functions. Its most important function is to protect the gel 12 from dirt and damage. In addition, it helps the gel 12 to remain in contact both with the pouch 1, and with the skin 10 surrounding the wound area. By adding extra support, it reduces the possibility of friction or shear when the patient is mobile. It also provides aesthetic value by providing a cosmetic cover for the wound area.

As can be seen from the foregoing, the installation of the pouch 1 in a wound cavity 11 is a relatively easy procedure. The pouch 1 can be rapidly and easily inserted into a wound cavity 11, and conformed to the shape of the wound cavity 11. The viscous nature of the gel 12 allows it to be rapidly and easily installed without the pain and discomfort associated with prior art drapes. Finally, the external drape 13 can be easily applied without the necessity for precision and re-installation which often happens with prior art drapes. Once the pouch 1 is installed in this manner, the CWDS system is ready to begin withdrawing exudates from the wound on a continuous basis.

The wound treatment system of FIGS. 1-5 provides a soft flexible system which can be installed within the wound in a rapid manner, and with minimal attempts to position the pouch 1. This results in a substantial reduction in pain and discomfort experienced by patients as compared to the installation of prior art dressings. The ease of installation also allows the single medical care provider to install the dressing without requiring assistance from second party. The beads 8 provide active antimicrobial treatment of wounds which accelerates the healing process. In addition, the shape and the flexibility in the structure of the pouch 1 allows the pouch 1 to be in contact with the entire wound cavity which increases drainage capability and healing speed. The multi-tubing 2 allows the delivery of medications without disturbing the wound dressing. The use of a nonporous upper surface 3 in combination with a porous lower surface 6 in the pouch 1 allows exudates to be pulled into the pouch 1 without subsequent leaking to the outer surface of the pouch 1. The structure of the tubing and the location of the perforations further provides a dispersed negative pressure which improves the process of removing exudates from the wound area which in turn increases the rate of healing.

FIG. 6 is a block diagram which illustrates the components of the drain/suction unit 14. The drain/suction unit 14 has several components. A power supply 15 is provided to power the various components of the device. In the preferred embodiment, the drain/suction unit 14 is battery operated to provide patient mobility. A CPU 16 controls the various functions of the device and allows the patient or medical care provider to turn on and off various functions such as the application of vacuum or the injection of medication. For ease of discussion, electronic control circuitry is referred to as CPU 16. However, CPU 16 may be a microprocessor, controller, or specialized fixed purpose circuitry, etc. Its only requirement is that it be able to control the various functions of the CWDS system. Also shown in this figure is the pump 17 which provides negative pressure to the pouch 1. The exudates pulled through the tubing 2 by the negative pressure would first be pulled into the drain/suction unit 14 at entry conduit 20. The exudates would enter the collection canister 19 from entry conduit 20 where they would be trapped. The negative pressure is applied to the collection canister 19 via conduit 21 that is attached to pump 17. Pump 17 may also be turned on and off under control of CPU 16 by solenoid 18. Those skilled and the art will recognize that some of these components can be merged together. Therefore, this figure is intended to illustrate functions provided by the drain/suction unit 14, and not necessarily the discrete components used to fabricate it.

Figure 7:
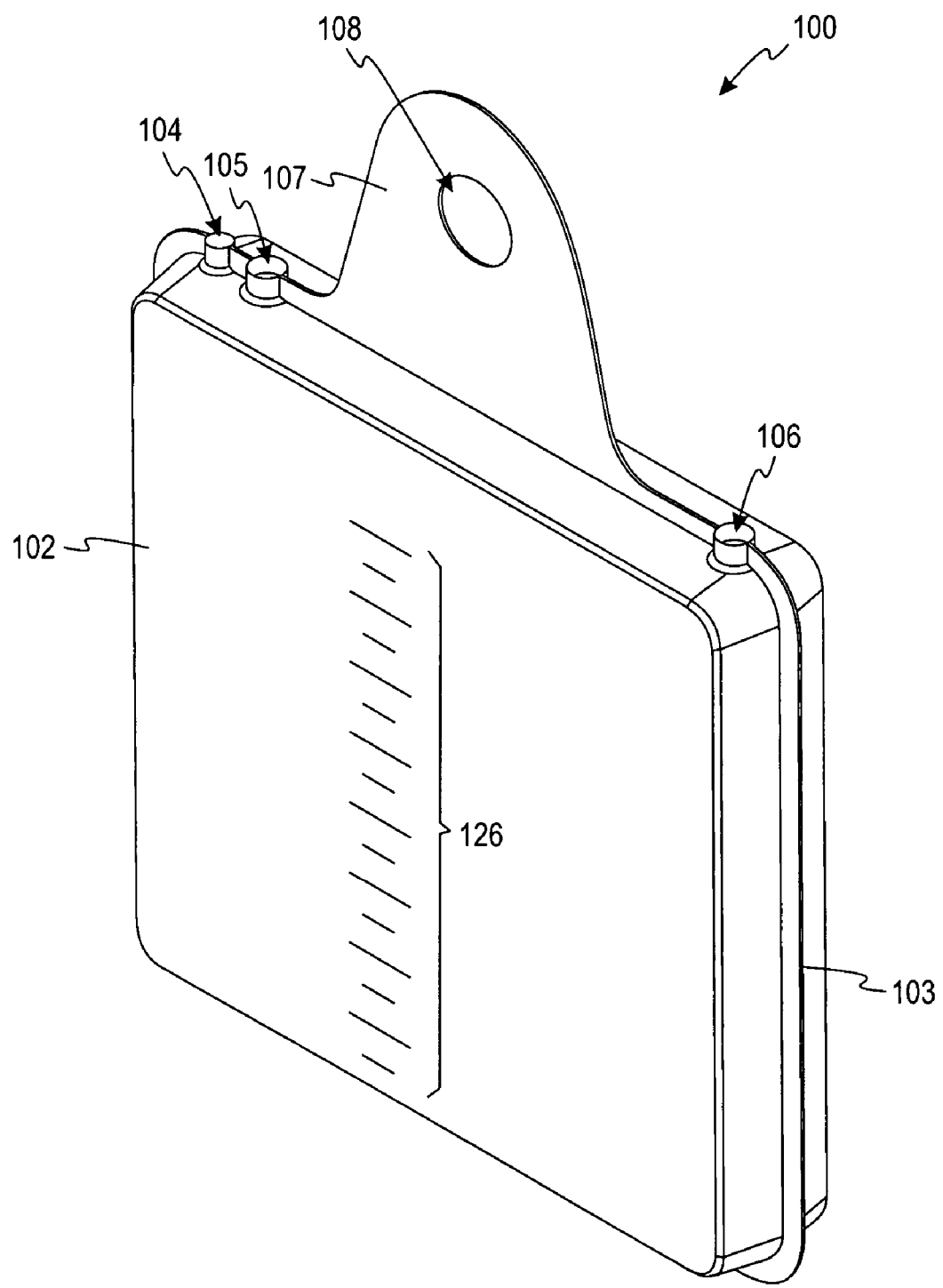
FIG. 7 illustrates a perspective view of a preferred embodiment of a wound exudate collection bag (WECB).

FIG. 7 illustrates a preferred embodiment of a wound exudates collection bag the ("WECB") 100 used by the invention. The WECB 100 stores the exudates and body fluids collected via suction. In this figure, a perspective view of a disposable collection bag 102 is shown. The collection bag 102 is fabricated from a non porous material that is completely water proof or spill proof from its content. The material used to fabricate the collection bag 102 can be any material which is suitable for the purpose of preventing leaks. For example, a shell of the collection bag 102 can be PVC, polyurethane, etc. The only requirement is that once exudates are in the collection bag 102, they will not leak out. The preferred collection bag is constructed of 10-mil urethane sheet which is RF welded into a rectangular bag having two ports to which the tubing is attached. The urethane is a translucent which allows the caregiver to see the color of the exudates. Pockets may be provided on the sides of the bag to slide over a mounting bracket on the controller, to secure the bag to the controller, and/or for hose management.

The collection bag 102 is preferably soft-sided so that it is more comfortable for the patient and less likely to cause a pressure point while in contact with the patient. The bag can be either hung from the vacuum source or attached to the patient's body close to the wound site.

Those skilled in the art will recognize that while a particular shape is shown for the collection bag 102 in this figure, the bag can be made in any suitable size and shape that is suitable for a particular wound size and shape. Further, the size of the collection bag 102 can vary depending on the amount of drainage or exudates expected from a given wound. Likewise, any suitable material can be used to fabricate the collection bag 102 which accomplishes goals of this invention.

Figure 11:
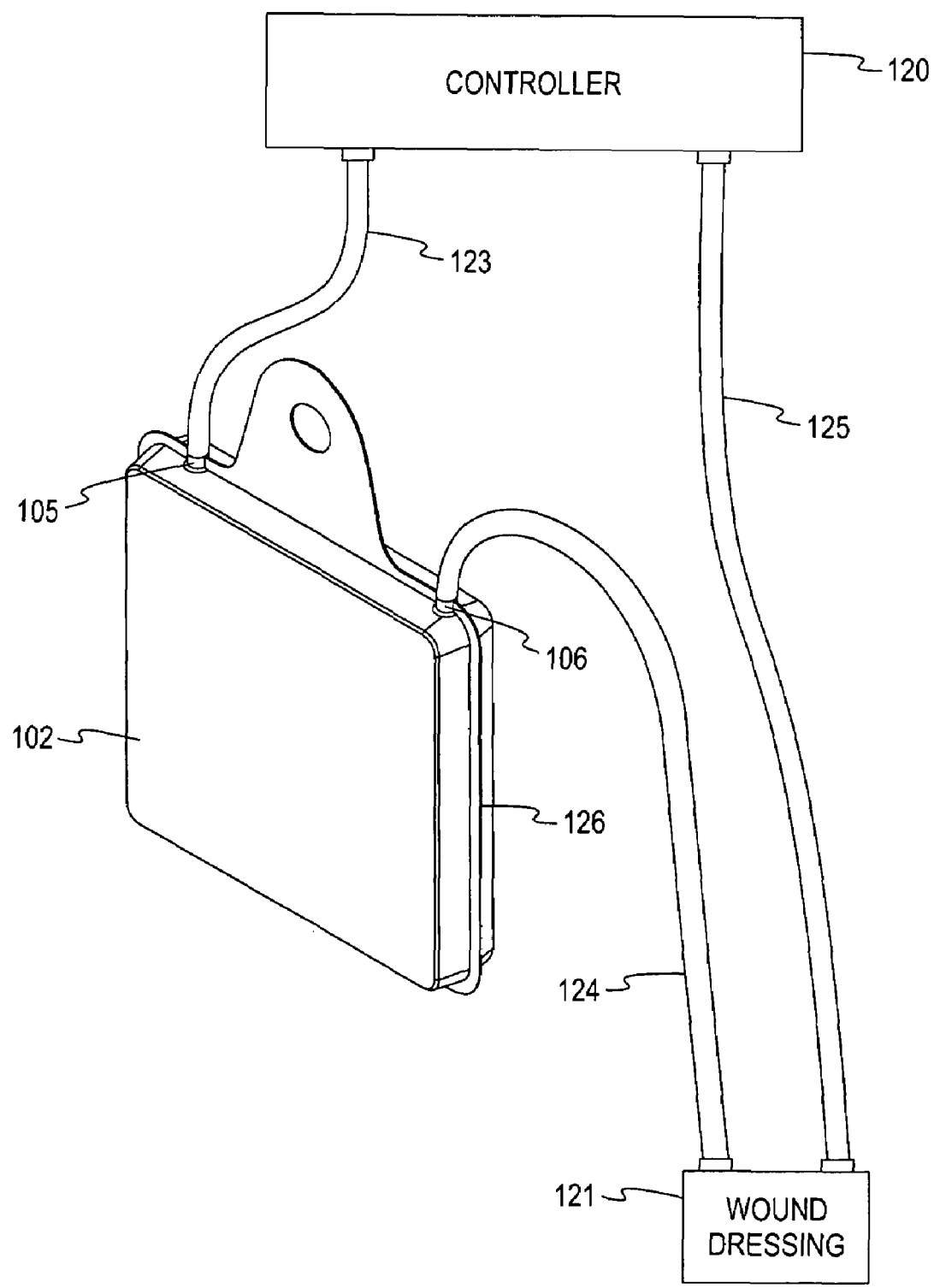
FIG. 11 illustrates a WECB 1 integrated into a WECB system which includes an external wound dressing, an external vacuum pump, an external pressure sensor, and associated tubing.

Also shown in FIG. 7 is a pressure connector 104 which attaches to a pressure sensor tube 122 (shown in FIG. 11), a vacuum connector 105 which attaches to a vacuum tube 123 (shown in FIG. 11), and an exudate connector 106 which attaches to an exudate tube 124 (shown in FIG. 11). The pressure connector 104 and the pressure sensor tube 122 allow a remote sensor 119 (shown in FIG. 11) to monitor the internal pressure in the collection bag 102, which indirectly allows the system to estimate the contents of the collection bag 102. The vacuum connector 105 and the vacuum tube 123 allow an external vacuum pump 120 to apply negative pressure to the inside of the collection bag 102. The exudate connector 106 and the exudate tube 124 provide a path for exudates from the wound dressing 121 to be pulled into the collection bag 102 by the negative pressure.

Also shown in this FIG. 7 is an attachment flap 107 which has an aperture 108. The attachment flap 107 and the aperture 108 allow the patient to attach the collection bag to any convenient place, such as a belt, a bedpost, etc. Of course, the attachment means exemplified by the attachment flap 107 and the aperture 108 can be accomplished by any number of known attachment means. In addition, the collection bag 102 has graded imprints 126 on one or both sides. The graded imprints 126 are a visual indicator showing the amount of exudates in the collection bag 102. While the total number of units indicated by the graded imprints 126 will vary depending on the size of the collection bag 102, a typical collection bag 102 will hold approximately 100 cc of exudates.

Figure 8:
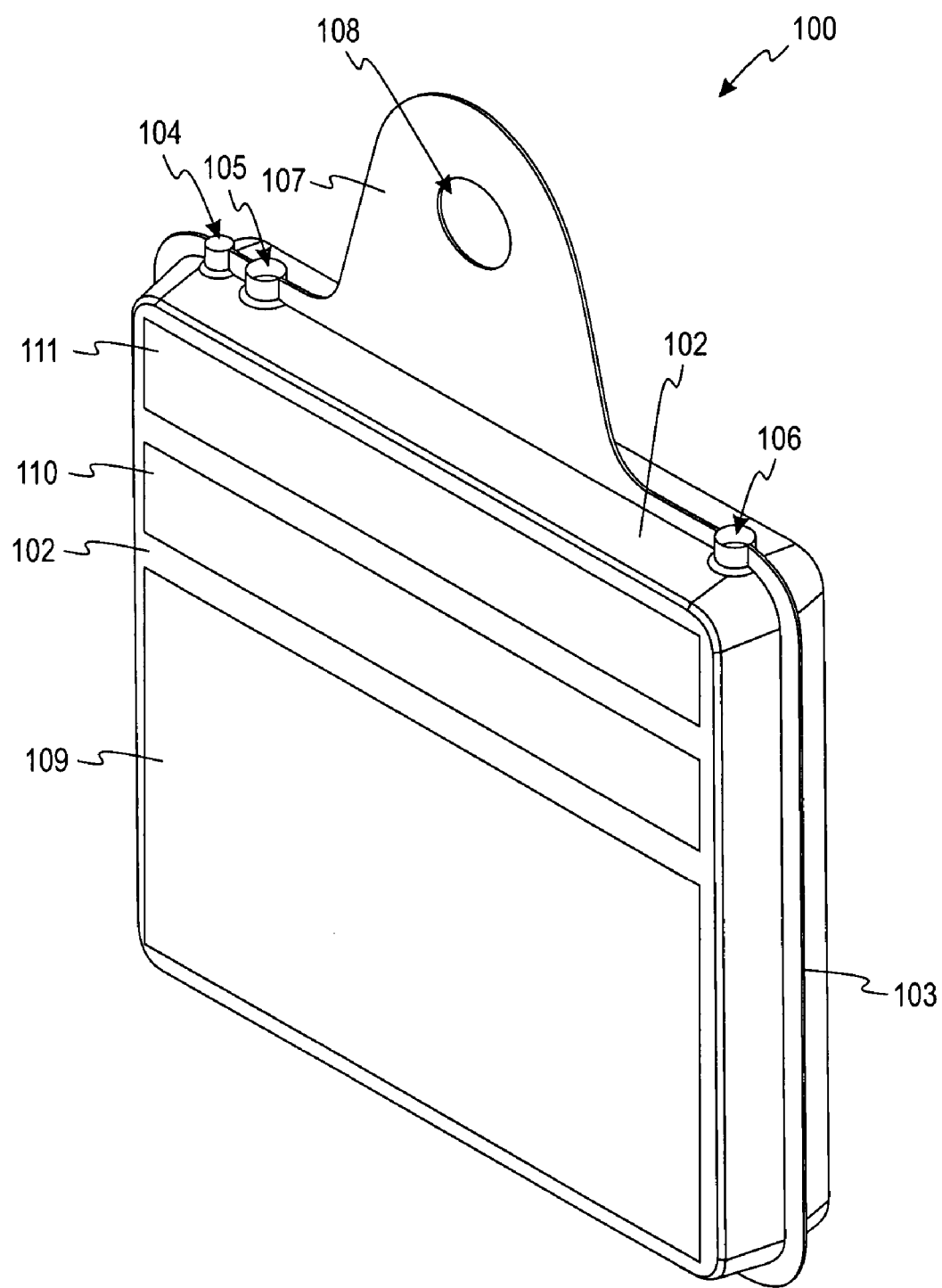
FIG. 8 illustrates a perspective view of a preferred embodiment of a WECB which is marked to show the relative positions of the lower storage compartment, the new chamber, and the upper chamber.

FIG. 8 illustrates the preferred embodiment of FIG. 7 with the following exception: outlines 109-111 are drawn on the side of the collection bag 102. Outlines 109-111 are shown for illustrative purposes only and would not appear on an actual collection bag 102. Outline 109 illustrates the general location of the lower storage chamber which is used for storing exudates. Outline 110 illustrates the general location of the middle chamber which is used for sensing pressure. Outline 111 illustrates the general location of the upper chamber which is used to provide negative pressure.

Figure 9:
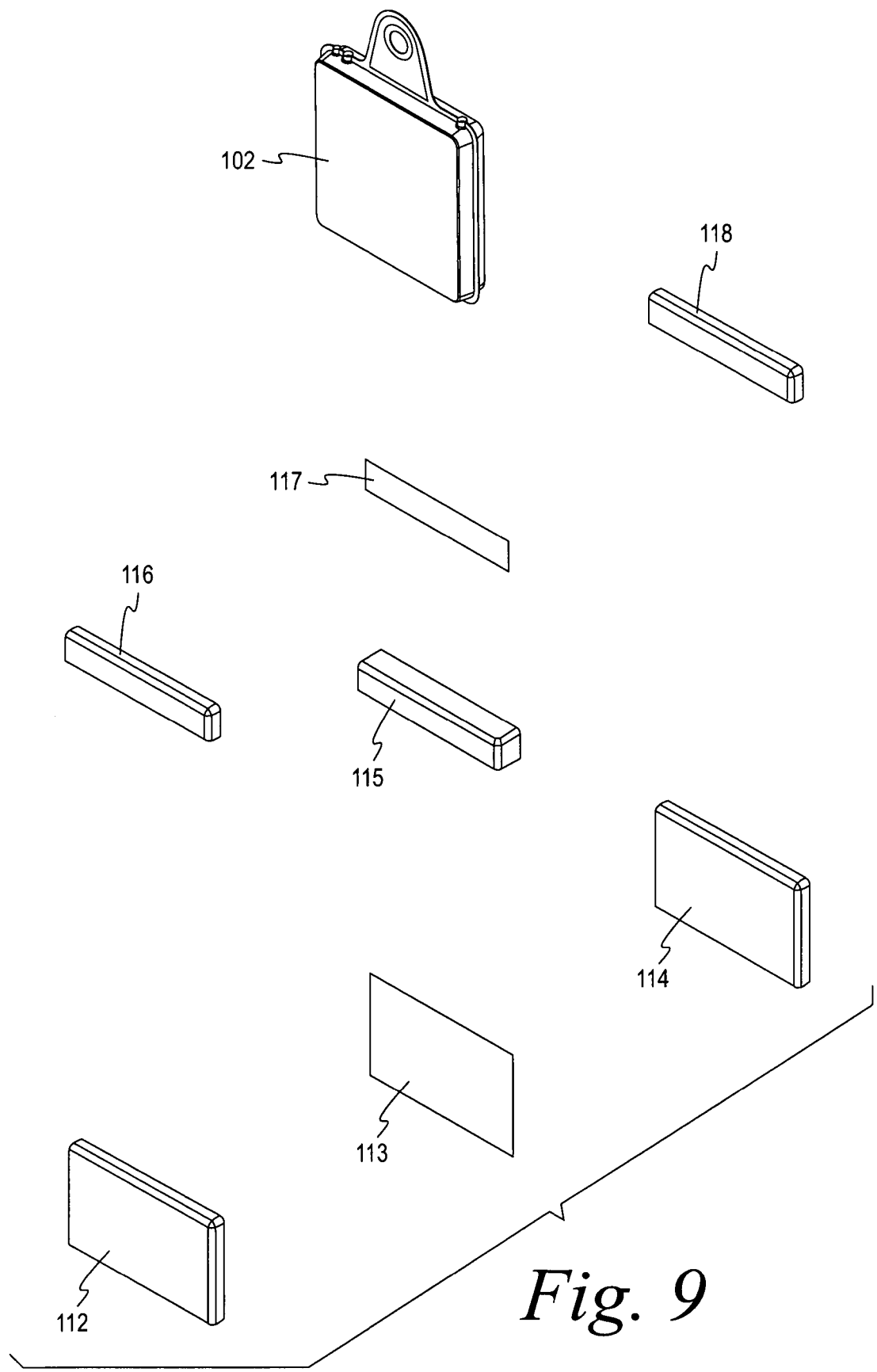
FIG. 9 illustrates a perspective view of a preferred embodiment of a WECB which also shows an exploded view of the internal components of the WECB.

FIG. 9 illustrates a perspective view of a preferred embodiment of the collection bag 102, and also shows, below the collection bag 102, the internal components which are inside the collection bag 102. The internal components preferably include an absorbent material 113 which is used to gel liquid exudates to prevent them from leaking from the collection bag 102. The absorbent sheet or powder provides an excellent and quick gelling capability to the exudates, thereby preventing bag spillage or any biohazard leakage from the bag. The absorbent material 113 can be fabricated from a number of commercially available fast absorbing sheet or powder materials which can retain many times their weight of liquid. The absorbent material 113 is sandwiched between two spacer layers 112, 114. In the preferred embodiment, the spacer layers 112, 114 are fabricated of porous nylon based material known as 3 dimensional spacer knitted fabrics. The purpose of the spacer layers 112, 114 is to prevent the inner walls of the collection bag 102 collapsing during the negative pressure which is generated by vacuum pump 120.

In a preferred embodiment of the illustrative collection bag, there are at least two mediums in the bag which contain the fluids collected. One medium is any absorbent material such as cotton terry cloth-like material or material which has open-cell, omni-directional pore structure. These materials wick and absorb the fluid as it comes out of the port openings in the bag. The second medium is any sort of gelling agent that transforms water into a thick gel. The gelling agent can be in the form of commercially available powders or sheets, or incorporated into fluffy batting sheets of polyester, cotton or similar materials. The purpose of the two mediums is to (1) wick and adsorb the liquid and have it evenly distributed inside the bag in order to obtain maximum gelling of the liquid and (2) gel the liquid so it has no opportunity to run up the hose prematurely, hit the filter, and shut the system down. Only when the bag is full will the liquid run up the hose and shut the pump off.

When negative pressure is applied to the collection bag 102, exudates are drawn from the wound dressing 121 through the exudate to 124 to the exudate connector 106. In the preferred embodiment, the exudate connector 106 includes an extension inside the collection bag 102 which draws the exudates to the bottom of the lower storage chamber.

The absorbent material 113 and the spacer layers 112, 114 comprise the main components of lower storage chamber defined by outline 109, above.

Above the lower storage chamber is the middle chamber. The middle chamber is occupied by a high-density foam barrier strip 115. The purpose of barrier 115 is to distribute the negative pressure to the lower storage chamber, and to provide a location to measure the pressure level inside the collection bag 102 for the purpose of estimating the fullness of the collection bag 102. Typically, a tube (not shown) will extend from the pressure connector 104 into the barrier 115. As the collection bag 102 fills, the pressure required to pull exudates into the collection bag 102 will increase. The pressure sensor 119 will correlate the amount of pressure to a figure which represents the approximate fullness of the collection bag 102. In this example, the barrier 115 is approximately 1"×1"×4" and sits above the lower storage chamber. Of course, those skilled in the art will recognize that the dimensions of barrier 115 will vary with the size of the collection bag.

The upper chamber includes spacer layers 116, 118 which sandwich an upper layer of absorbent material 117 in the same manner as was done in the lower storage chamber. Negative pressure applied by the vacuum pump 120 will pass through the spacer layers 116, 118 and apply pressure to the middle chamber and lower storage chamber. Absorbent material 117 is used to absorb any overflow.

Figure 10:
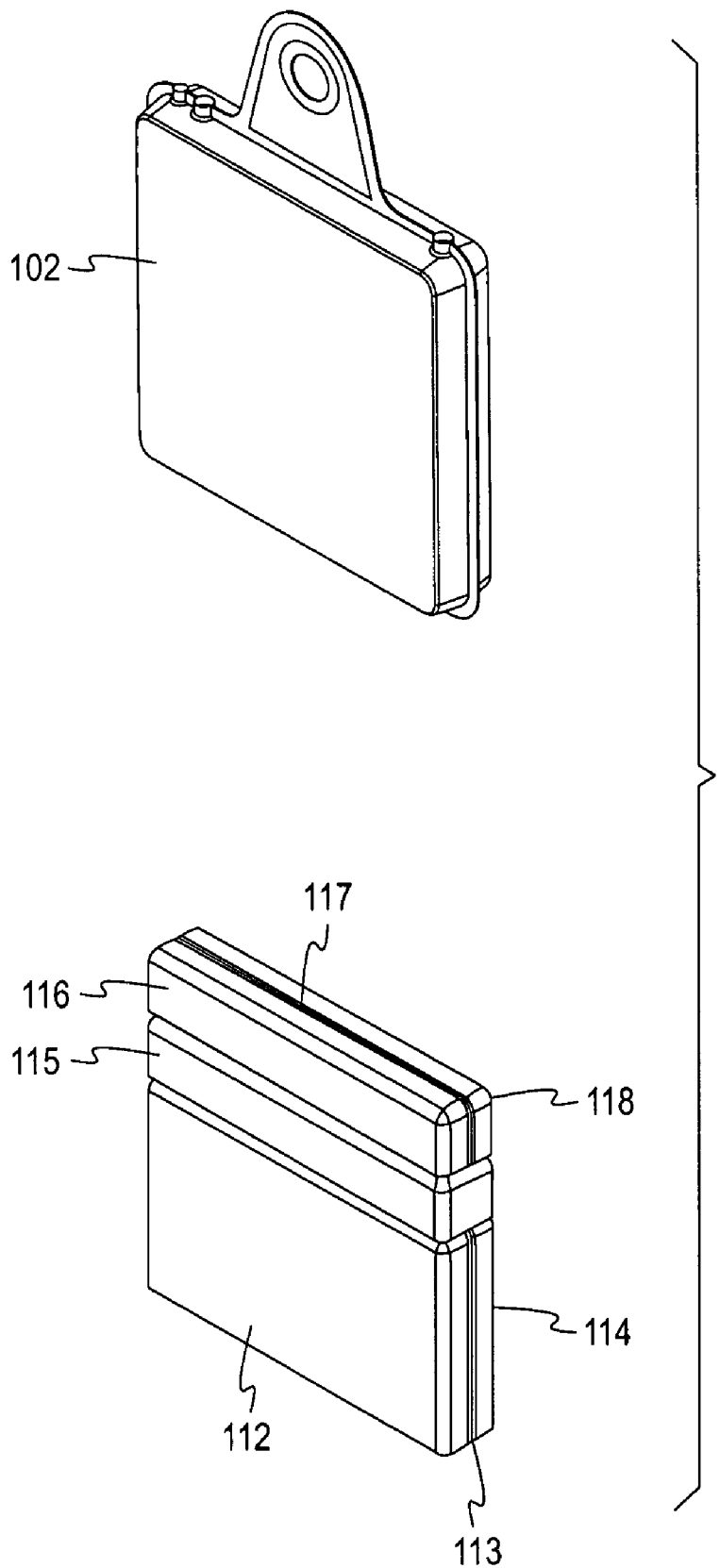
FIG. 10 illustrates a perspective view of a preferred embodiment of the WECB which shows the internal components assembled together prior to insertion into the WECB.

FIG. 10 illustrates the internal components (which were discussed above in regard to FIG. 9) of the collection bag 102 in an assembled configuration prior to installation inside the collection bag 102.

FIG. 11 illustrates how the collection bag 102 is used in conjunction with the other elements of the system. A wound dressing 121 is shown connected to the collection bag 102 via an exudate tube 124. During operation, exudates are drawn from the wound dressing 121 through exudate tube 124 into the lower storage chamber of the collection bag 102. Also shown in this figure is a controller 120 that includes the vacuum pump, which applies negative pressure to the upper chamber of the collection bag 102 via vacuum tube 123. Pressure inside the collection bag 102 is measured by a pressure sensor, also contained in the controller 120 and connected to the vacuum pump. When the pressure inside the collection bag 102 is measured by the pressure sensor 119 and is determined to be above a predetermined level, the pressure sensor produces a signal that causes the vacuum pump to shut down. The shutdown will prevent the collection bag 102 from overflowing. A hydrophobic filter is also preferably connected to the controller end of the tube 123 to prevent any liquid from entering the controller once the collection bag is full.

A third tube 125 connects to the controller 120 at one end (and has a hydrophobic filter at this end also) and connects to the wound dressing 121 at the other end. This tube 125 typically has a smaller diameter than the other two tubes, and allows a small amount of air from the controller to enter the wound site during preselected intervals for the purpose of modulating the negative pressure applied to the wound.

Those skilled in the art will recognize that a collection bag 102 can be fabricated in a variety of suitable configurations. In the preferred embodiment, the collection bag 102 is fabricated with front and rear sides, and sealed along a seam 126, as shown in FIG. 11. The seam 126 should be sealed to prevent any leakage. Any suitable sealing material can be used. In the preferred embodiment, the sealing material is preferably a hydrocolloid, a silicone, or a lyogel, such as a hydrogel, which are easily deformable.

For illustrative purposes, tubes 122-124 are shown in the drawings as separate units. However, for ease of use in a finished product, the single lumen tubes can be replaced with a multi-lumen structure which will allow a patient or health provider to more conveniently disconnect a filled collection bag 102, and replace it with a new collection bag 102. In a preferred embodiment, the entire WECB 1 system is a portable unit which will allow the patient to have mobility. A portable WECB 1 system can be attached to the patients clothing. The portable pump 120 is preferably a portable battery powered device. The pressure sensor 119 can be physically integrated with the pump 120. Likewise, the pump 120 and the pressure sensor 119 can be held by a pouch (not shown) which can also provides storage to hold the WECB 1.

Figure 12:
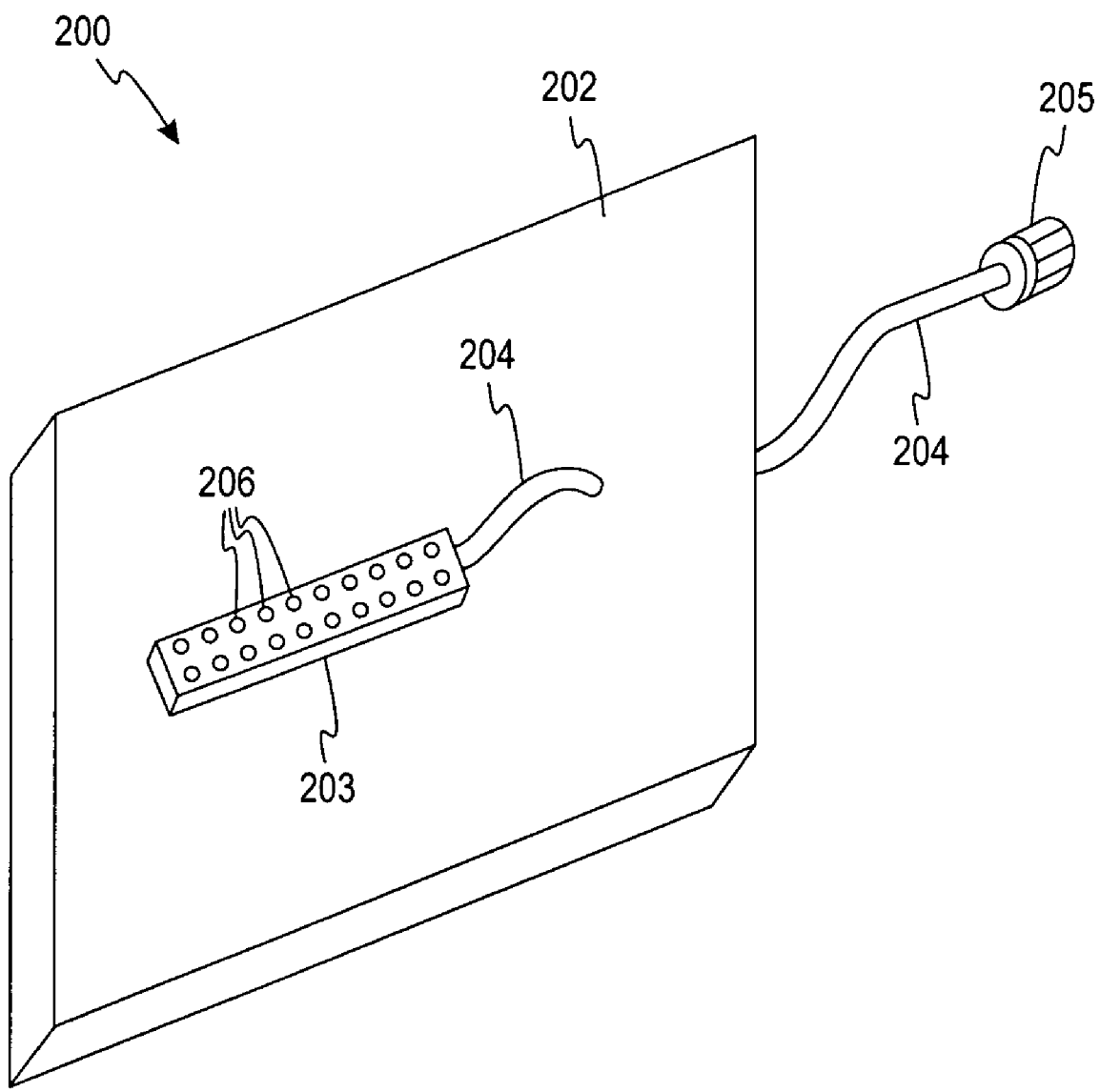
FIG. 12 illustrates a perspective view of a preferred embodiment of the wound dressing patch. This view illustrates the surface of the patch which contacts the patient's skin.

FIG. 12 illustrates a perspective view of a modified wound dressing patch system 200. This view illustrates the inner surface 202 of the patch 200 which contacts the patient's skin. In the preferred embodiment, the patch 200 is made from a pliant material that is capable of conforming to the surface contours of a patient's skin. Flexibility is important because it allows the patient greater freedom of movement with a reduced risk of becoming detached from the surface of the patient's skin. In addition, the flexible nature of the patch reduces the risk of leakage around the periphery of the patch. In the preferred embodiment, the patch 200 is fabricated from material that has a gel-like feel to provide the greatest patient comfort. Of course, the patch 200 should prevent any exudate leakage, to prevent any external contamination. However, any suitable material can be used to fabricate the patch 200 so long as it accomplishes the goals and objectives of the invention. The inner surface 202 may have a layer of adhesive to secure it to the surface of the patient's skin.

Also shown in this figure is a drain 203 that has a plurality of apertures 206 that are used to withdraw exudates from a patient's wound. Exudates are drawn under negative pressure through a tube 204 to a connector 205 that is attached to a conventional vacuum pump (not shown). By routing the tube 204 through the wall of the patch 200, the tube 204 does not interfere with the peripheral edge of the patch 200 when it is secured to the patient's skin. As a result, the probability of leakage is reduced. A further advantage associated with the use of pliant gel-like material to fabricate a patch 200 is that if the patch 200 is made sufficiently thick, it will snugly fit around the outer surface of the tube 204. This also helps to reduce the possibility of exudate leakage. Of course, when the wound dressing patch 200 is fabricated, the tube 204 can be sealed to the patch to ensure that no exudate leakage occurs. The prefabricated nature of the patch eliminates the time required for medical personnel to apply the wound drain dressing to a patient. The quicker installation is facilitated by the fact that all components of the dressing are incorporated into a single device, so that the entire dressing can be applied in a single step.

Figure 13:
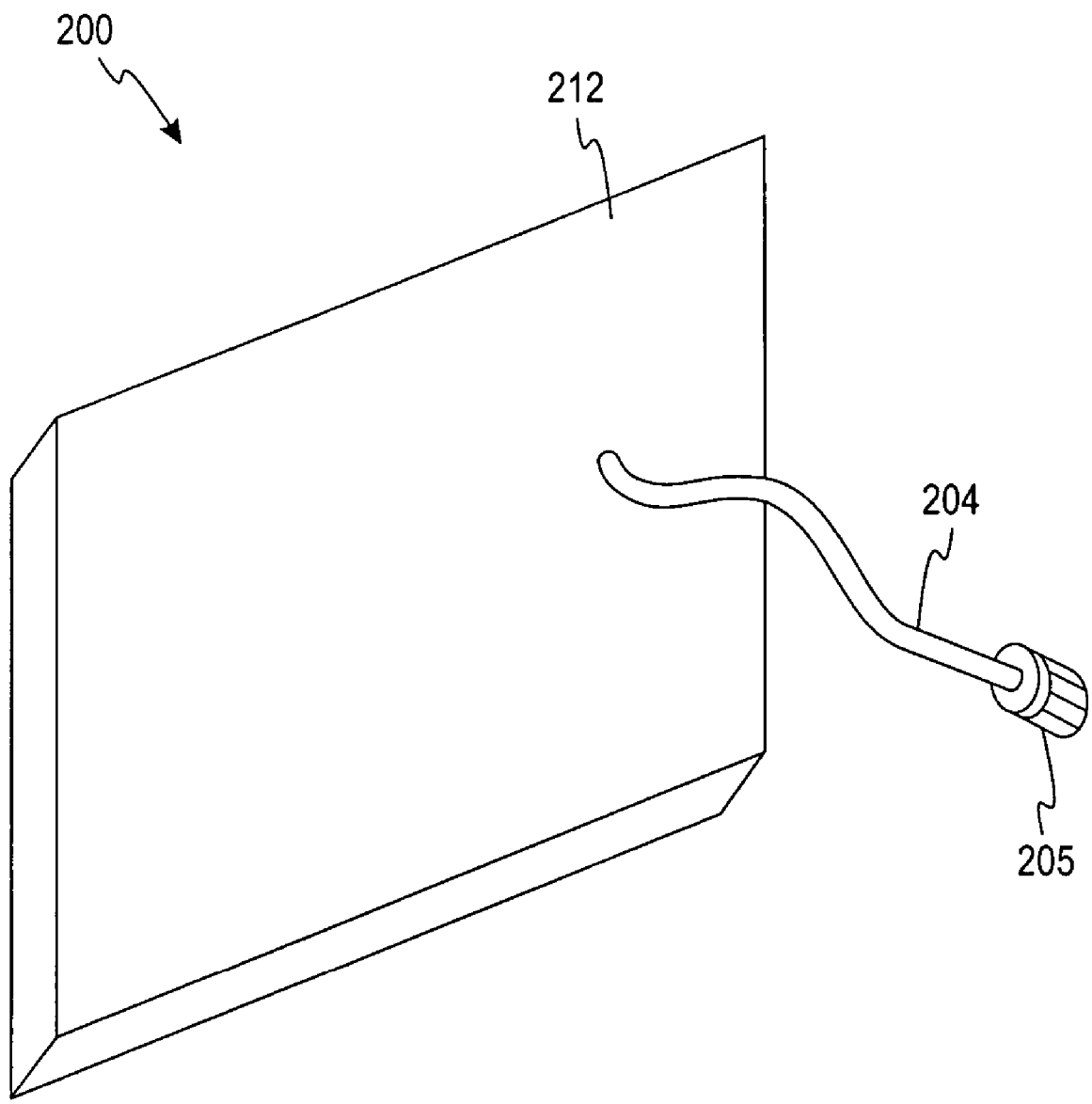
FIG. 13 illustrates a perspective view of a preferred embodiment of the wound dressing patch. This view illustrates the surface of the patch which does not contact the patient's skin.

FIG. 13 illustrates a perspective view of the wound dressing patch 200. This view illustrates the outer surface 212 of the patch 200 which does not contact the patient's skin. The tube is shown extending from the outer surface 212 to the connector 205.

Figure 14:
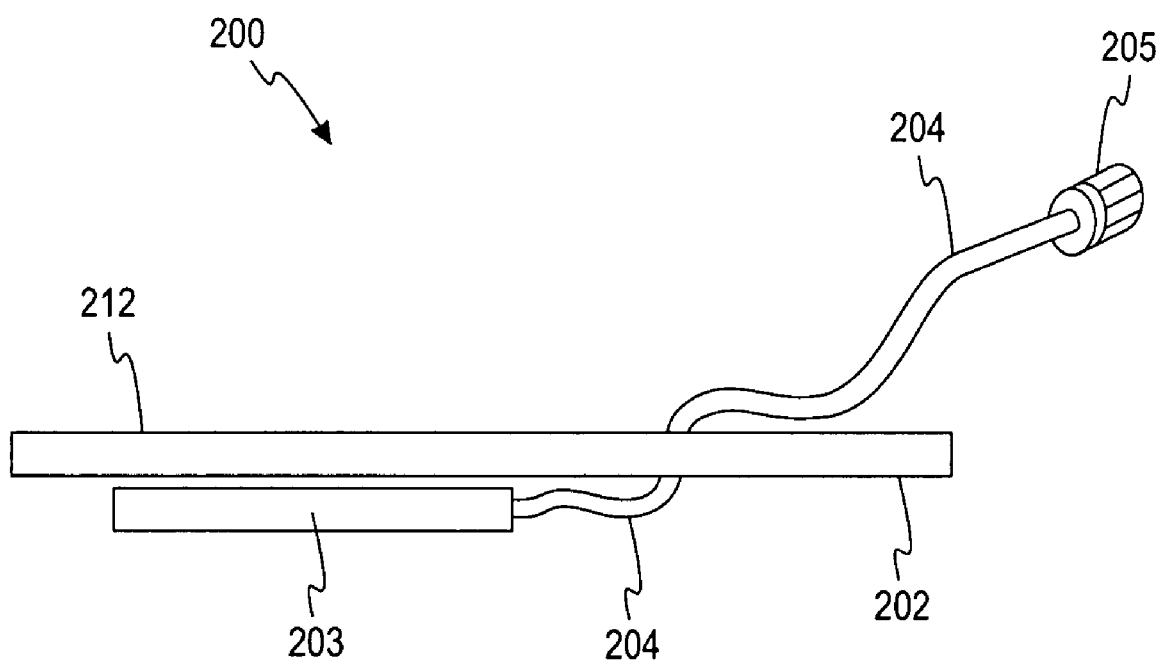
FIG. 14 illustrates a side view of a preferred embodiment of the wound dressing patch. This view illustrates the position of the wound drain in relation to the patch and also illustrates the drain tube inserted through the wall of the patch.
Figure 15:
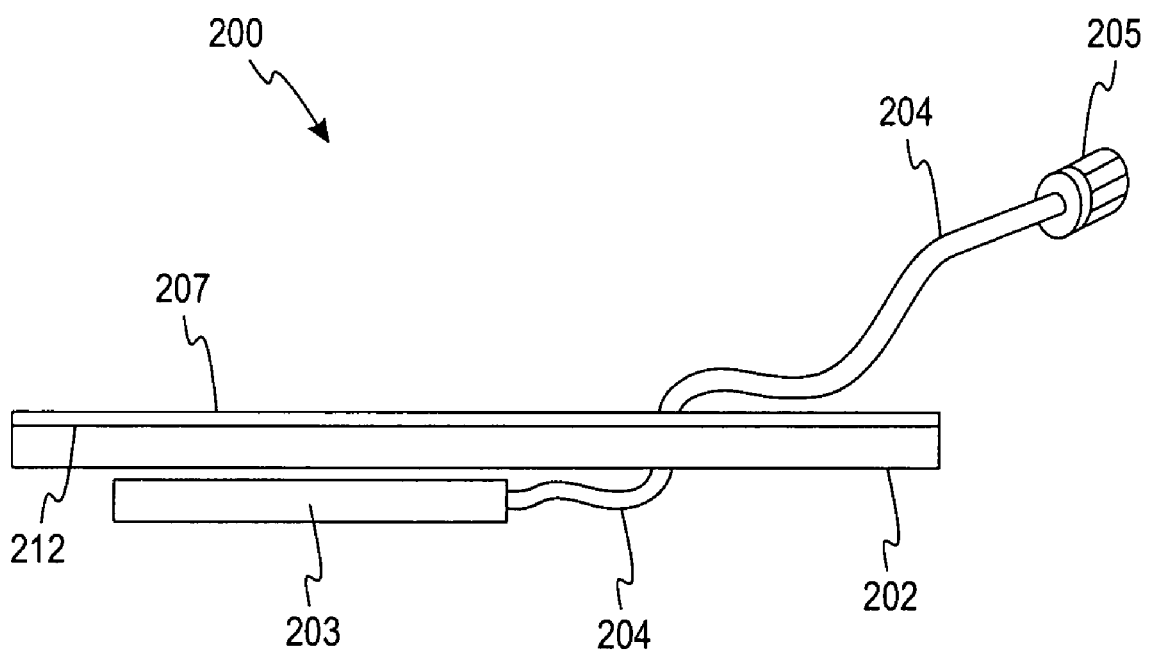
FIG. 15 illustrates a side view of a preferred embodiment of the wound dressing patch. This view illustrates the position of the wound drain in relation to the patch and illustrates the drain tube inserted through the wall of the patch. In addition, a layer of bandage material is shown attached to the upper side of the patch.

FIG. 14 illustrates a side view of the wound dressing patch 200. This view illustrates the position of the wound drain 203 in relation to the patch 200 and also illustrates the drain tube 204 inserted through the wall of the patch 200. FIG. 15 illustrates a modified patch 200 that includes a layer of bandage material 207 attached to the upper side 212 of the patch 200.

Figure 16:
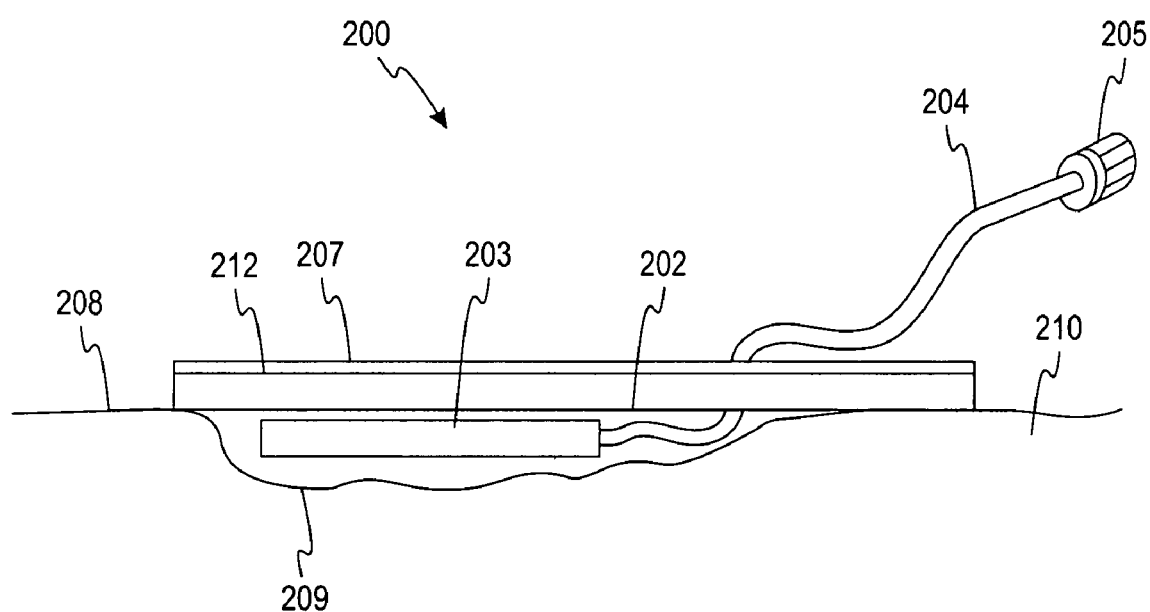
FIG. 16 illustrates a side view of a preferred embodiment of the wound dressing patch. This view illustrates the WDP installed over a patient's wound. The wound drain is shown inside of the wound, and the patch is secured to the surface of the patient's skin.

FIG. 16 illustrates a side cutaway view of the wound dressing patch 200 installed over a patient's wound 209. The wound drain 203 is shown in the wound 209, and the patch 200 is secured to the surface 208 of the patient's skin 210. As can be seen from this figure, the peripheral edge of the lower surface 202 of the patch 200 is secured to the patient's skin via adhesive. This figure also illustrates how the routing of the tube 204 through a wall of the patch 200 allows the tube 204 to avoid interfering with the sealing of the patch 200 to the surface 208 of the patient's skin 210.

Figure 17:
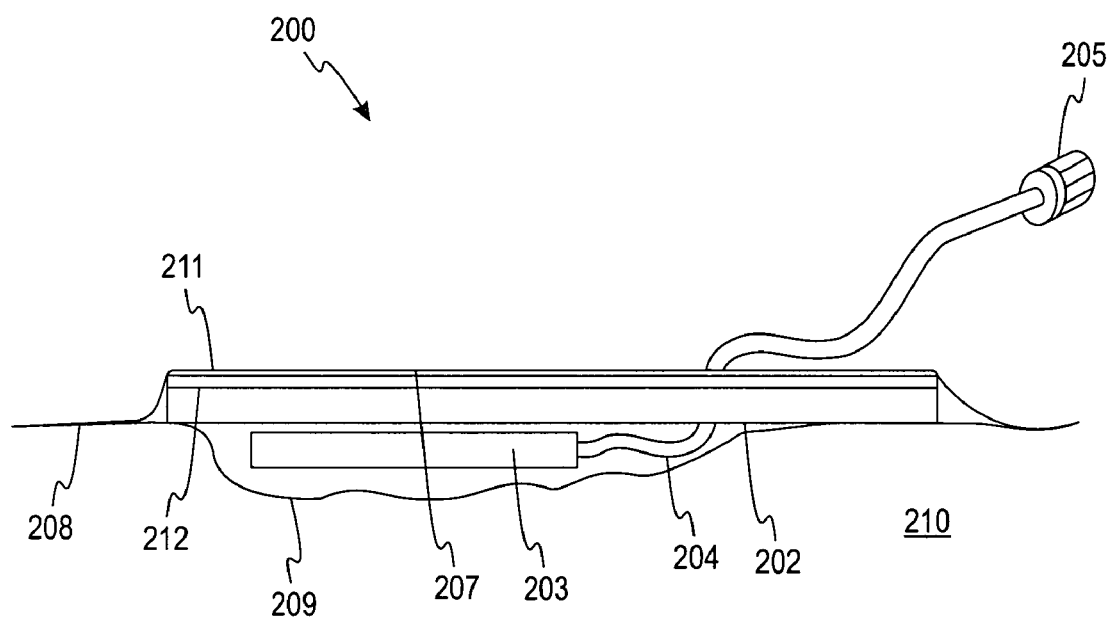
FIG. 17 illustrates a side view of a preferred embodiment of the wound dressing patch. This view illustrates the WDP installed over a patient's wound. The wound drain is shown inside of the wound, and the patch is secured to the surface of the patient's skin. A dressing cover is shown covering the outer surface of the WDP, and secured to the surface of the patient's skin.
Figure 18:
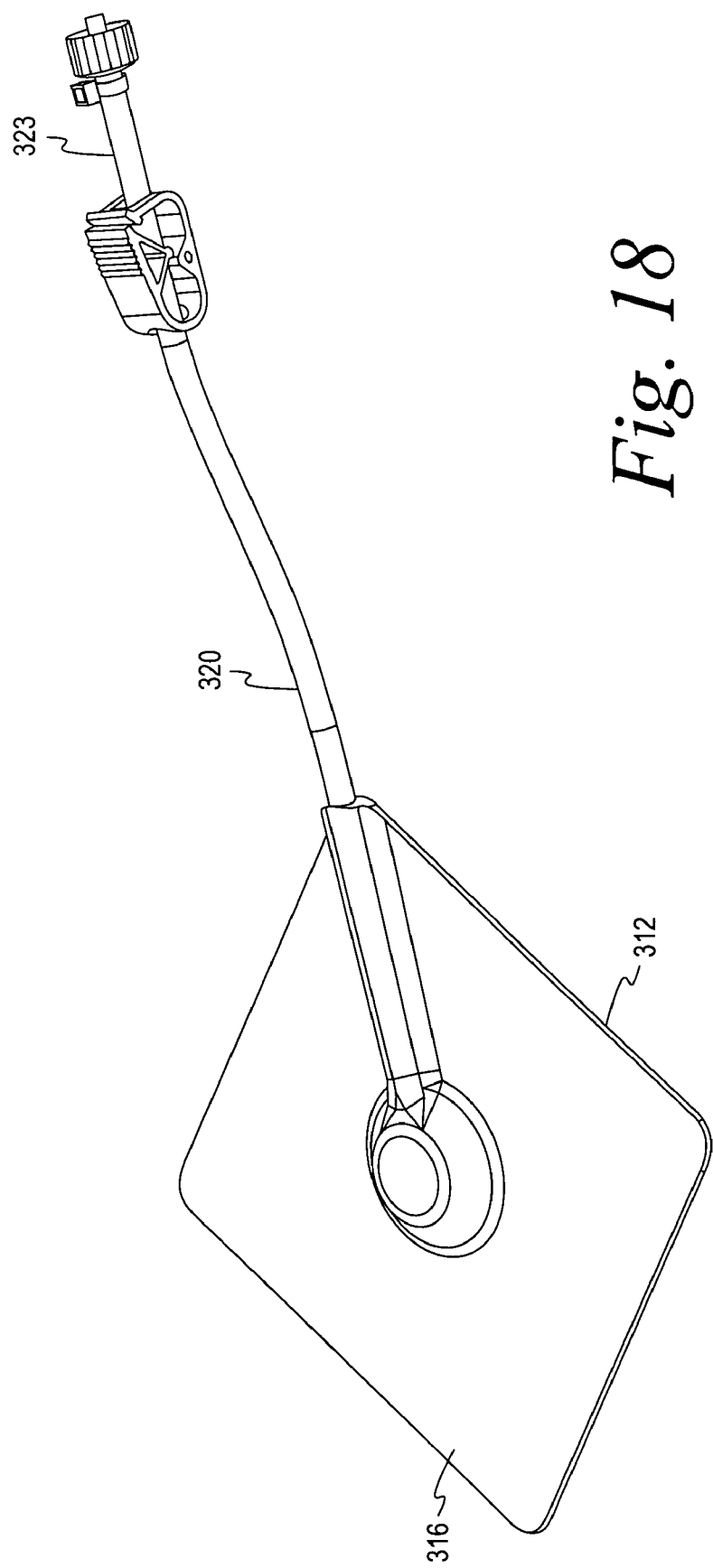
FIG. 18 is a top perspective view of a modified embodiment of a wound dressing for use in a wound drainage system.
Figure 19:
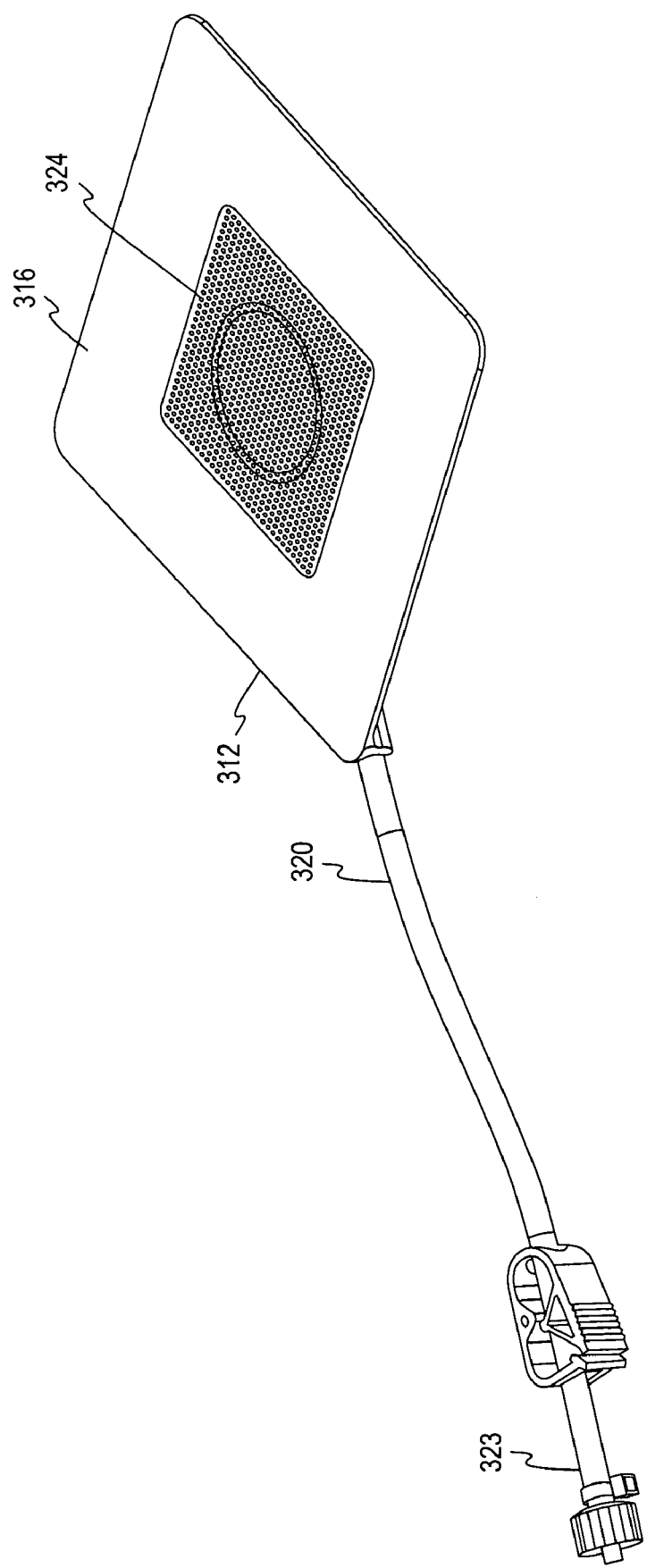
FIG. 19 is a bottom perspective view of the wound dressing of FIG. 18.
Figure 20:
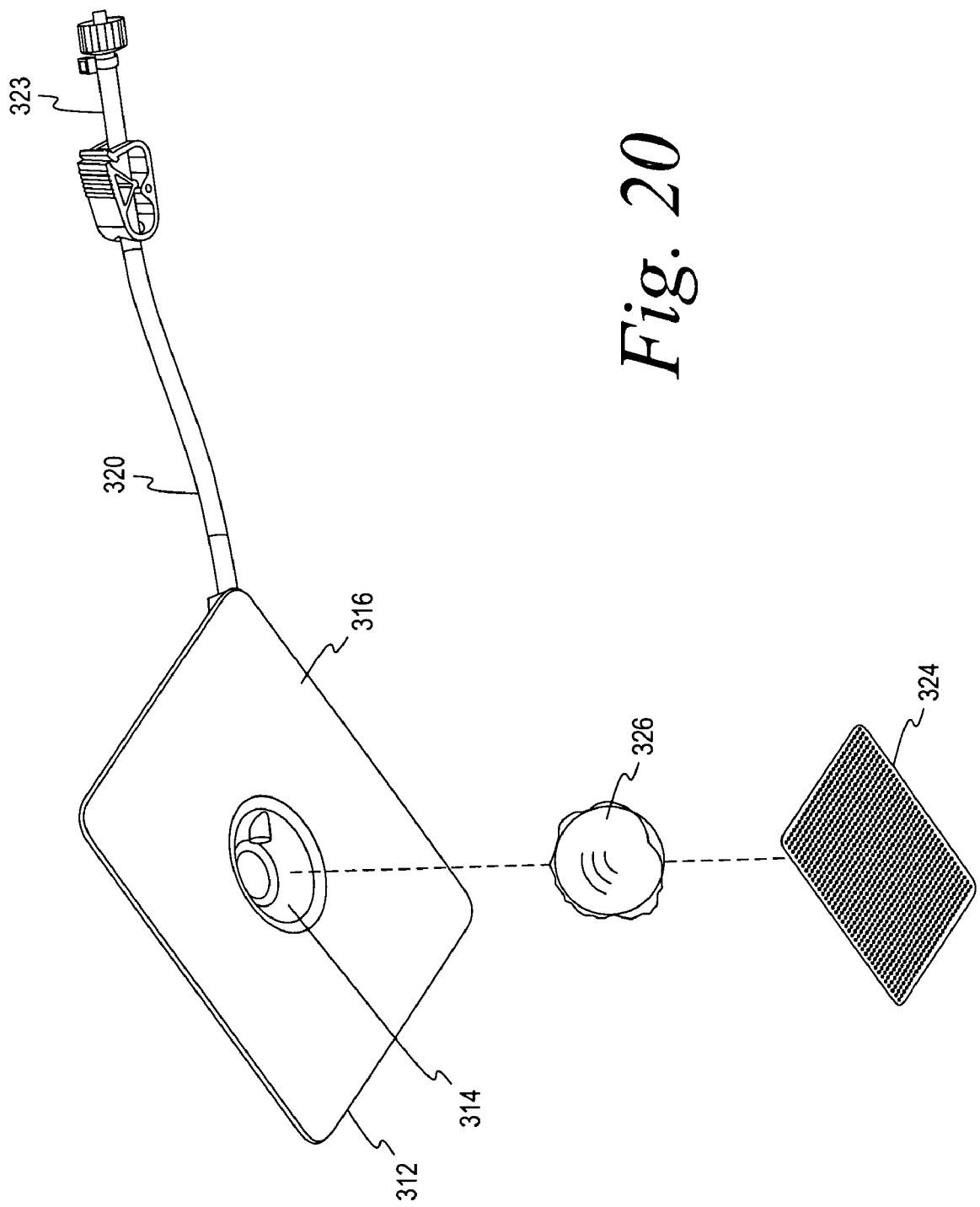
FIG. 20 is a partially exploded perspective view of the wound dressing of FIG. 18.
Figure 21:
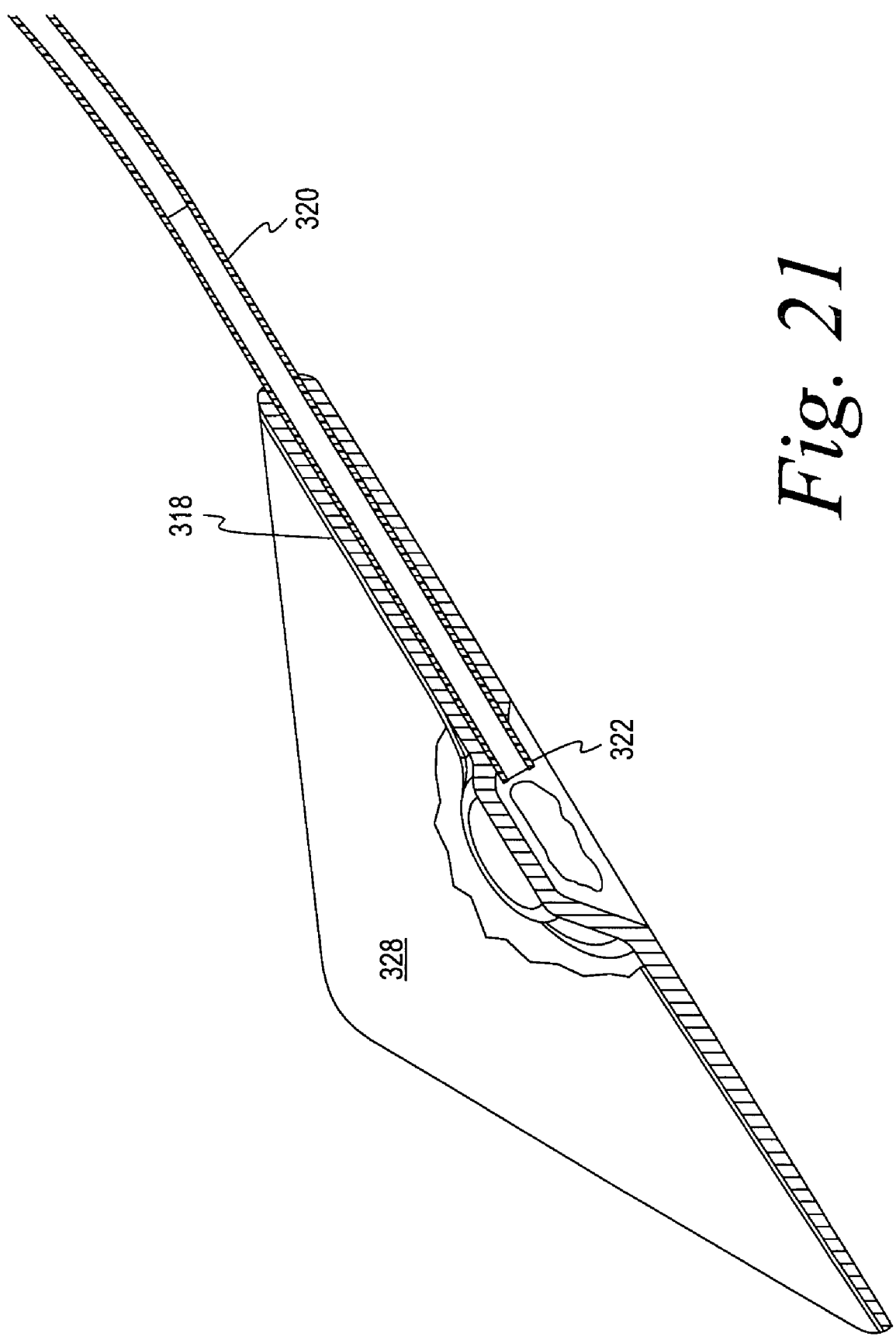
FIG. 21 is a section taken diagonally through a top perspective view of the wound dressing of FIG. 18.
Figure 22:
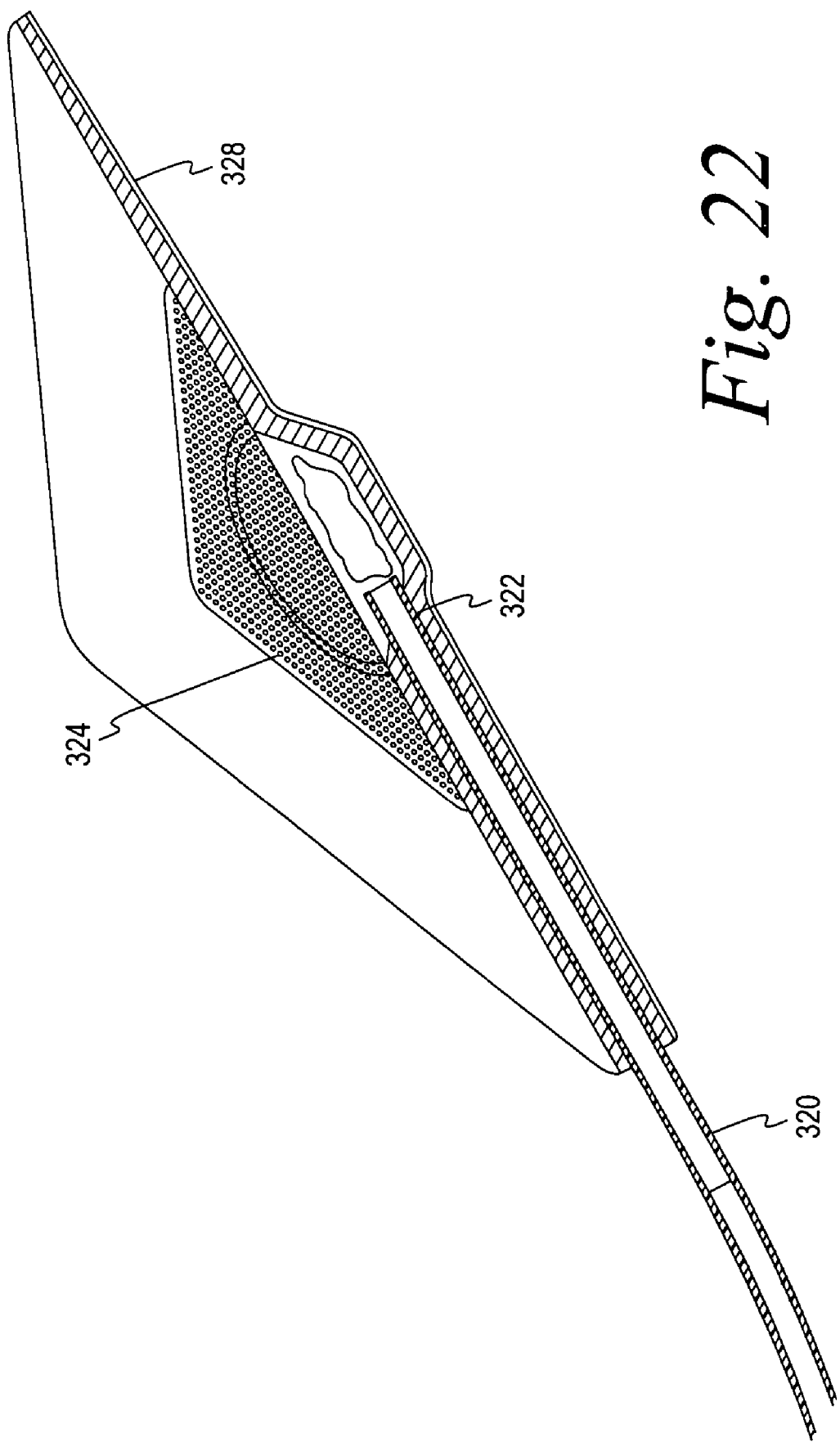
FIG. 22 is a section taken diagonally through a bottom perspective view of the wound dressing of FIG. 18.

Also illustrated in this figure is bandage material 207 that covers and protects patch 200 from environmental factors. In addition, it also provides a gripping surface to facilitate application of the patch to the patient's wound. Bandage material 207 can be fabricated from any suitable material which accomplishes the goals of the invention, such as cloth or synthetic material. FIG. 17 illustrates a cutaway side view of a modified patch that includes a dressing cover 211 that covers the outer surface of the bandage material 207, and is secured at its periphery to the surface 208 of the patient's skin 210. While the patch can be fabricated without an integral dressing cover 211, its convenience of use and ease of installation are improved by incorporating the dressing cover 211 into the patch. This allows the entire patch to be installed on a patient's wound in a single-step application.

Another modified wound dressing for use in a closed wound drainage system is illustrated in FIGS. 18-22. This dressing includes a gel sheet 312 that forms a cavity 314 opening through the lower surface 316 of the gel as well as into a tunnel 318 for receiving a drain tube 320. The drain tube 320 is inserted through the tunnel 318 with the distal end 322 of the tube extending slightly into the cavity 314. A porous sheet 324 is attached to the lower surface of the gel sheet 312 and covers the cavity opening in the lower surface of the gel. The cavity 314 is packed with a fibrous material 326 that is captured between the porous sheet 324 and the upper wall of the cavity 314. A protective material 328 is attached to the upper surface 330 of the gel.

The gel sheet 312 is applied directly to a patient's wound. The gel sheet is sized to cover an area larger than the wound, and the gel has a natural tackiness such that it sticks to the healthy skin surrounding the wound. By simply applying pressure to the gel, the gel adheres to the skin to form a seal sufficient to maintain a pressure differential between the ambient atmosphere and the internal space formed by the gel cavity 314 and the wound opening. The seal also prevents exudates from leaking out of the closed wound drainage system. The level of tackiness of the gel can be adjusted depending on the desired level of adhesion to the patient's skin surface. The gel is advantageous in that no adhesive is required to attach the gel to the patient's skin surface. The gel also assists in protecting the healthy skin by maintaining its moisture level while absorbing undesired, excess moisture from the wound site.

One suitable gel for use in this embodiment of the invention is commercially available under the name "Elasto-Gel" hydrogel wound dressing available from Southwest Technologies, Inc. in North Kansas City, Mo. This particular gel is a polymer matrix with a high glycerine content and is bacteriostatic and fungistatic. The basic gel is described in more detail in U.S. Pat. No. 4,671,267 issued Jun. 9, 1987 and entitled "Gel-Based Therapy Member and Method" which is incorporated by reference herein in its entirety. While not intending to be bound by any particular theory of operation, it is believed that the high glycerine content of this particular gel assists in maintaining the proper amount of moisture within the open wound and absorbing undesired, excess moisture.

The gel of U.S. Pat. No. 4,671,267 is a self-sustaining pliable gel. The gel material can be applied directly to injured skin to in effect create a temporary skin with ideal air permeability. The gel broadly includes a water soluble humectant entrapped within a polymeric matrix having therein acrylic acid or acrylamide monomer moieties. The gel has outstanding pliability and moisture sorbing properties over a very broad temperature range. The gel is characterized by the properties of maintaining its self-sustension and pliability over a relatively broad temperature range of from about −20° to 350° F. and of absorbing and desorbing moisture. The moisture absorbing and desorbing properties of the gel create a moisture equilibrium between the gel, damaged skin and the atmosphere, thus promoting rapid healing.

The gel includes a water soluble humectant entrapped within a polymeric matrix. The polymeric matrix preferably includes acrylic acid or acrylamide monomer moieties. The gel is a self-sustaining, non-flowable, pliable gel having a water soluble humectant entrapped within a polymeric matrix having therein acrylic acid or acrylamide monomer moieties. More specifically, the gel is a self-sustaining pliable gel that comprises from about 10 to 25% by weight synthetic polymeric matrix, from about 10 to 50% by weight water, and a substantial quantity of water soluble humectant entrapped within the matrix where the gel is characterized by the property of absorbing and desorbing moisture. The gel can have a wide variety of thicknesses, but generally speaking the gel should have a thickness of from about ¼ to 1½ inches.

While the preferred cross linking agent is N,N methylene-bisacrylamide (MBA), other types of cross linking agents can be employed such as N-methylolacrylamide, allyl methacrylate, and ethylene glycol dimethacrylate. Moreover, while ammonium persulfate is a suitable initiator for the polymerization reaction, the use of an initator is not essential. Finally, while acrylamide is the preferred matrix-forming material, other similar materials can also be used, such as acrylic acid.

Where acrylic acid is used in the gel, the acrylic acid should be used at a level of from about 10 to 20% by weight, humectant at a level of from about 20 to 80% by weight, water at a level of from about 20 to 70% by weight, N,N methylene-bisacrylamide (MBA) at a level of from about 0.01 to 0.04% by weight, and initiator at a level of from about 0.01 to 0.04% by weight. The most preferred ranges may also be from about 14 to 18% acrylic acid, from about 50 to 76% humectant, from about 8 to 22% water, and from about 0.01 to 0.3% cross linking agent.

The gel advantageously includes a humectant selected from the group consisting of glycerin, ethylene glycol, propylene glycol, dimethyl sulfoxide and dimethyl formamide. In addition, the humectant is preferably present at a level of from about 20 to 85% by weight in the gel body, and more preferably from about 50 to 75% by weight. The most preferred polymeric matrix is selected from the group consisting of polymers, copolymers, and terpolymers containing acrylic acid or acrylamide monomer moieties, and most preferably is a polymer of acrylamide.

Those skilled in the art will also appreciate that by proper selection of monomer and by varying the ratio of monomer (or monomers) relative to the cross linking agent and humectant, the hardness and toughness of the gel material may be altered and controlled. Accordingly, if relatively high moisture absorption characteristics are desired, the gel should be formulated to have a high percentage of humectant and a relatively low percentage of cross linking agent in order to produce a soft, relatively rubbery gel. If more firmness is required, the amount of humectant may be reduced, whereas the amount of cross linking agent should be increased.

The drain tube 320 extends into the cavity 314 in the gel so that the open distal end of the tube can receive fluids from the gel cavity. The tube-gel combination may be formed by pouring the gel in liquid form into a mold containing the tube 320 so that the tunnel 318 is molded directly onto the tube 320. Thus, the drain tube 320 is embedded in the gel and is entirely surrounded by the gel except for the distal end portion of the tube that opens into the cavity 314 and the proximal end portion of the tube that exits the outer end of the tunnel 320 for connection to a collection container and the vacuum pump.

The drain tube 320 may contain more than one lumen. For example, with a dual-lumen tube, one of the lumens may be connected to a vacuum or suction source while the other lumen is used for supplying air or medicine to the wound site. Alternatively, the drain tube may be used in combination with other tubes which can be used for purposes such as supplying air or medicine to the wound site.

The proximal end 323 of the drain tube 320 is connected to a vacuum or suction source (not shown) such as a vacuum pump to apply a negative pressure to the wound via the dressing. Once the vacuum source is applied, the gel forms an airtight seal with the healthy section of a patient's skin surface. The negative pressure that is applied to the wound site can be varied over a range of from about 1 millimeter of mercury (mm/Hg) to about 275 millimeters of mercury (mm/Hg) below atmospheric pressure. The desired negative pressure depends on factors such as the extent of the wound, the desired healing time, the clinician's specifications, the patient's pain tolerance level, and the patient's desired comfort level. A typical negative pressure is approximately 125 millimeters of mercury (mm/Hg) below atmospheric pressure.

The time period for use of the closed wound drainage system can vary from minutes to hours to days, e.g., from 12 hours up to or even exceeding 30 days. The desired time period for use of the closed wound drainage system will vary based on the nature of the wound, the clinician's recommendations, the healing rate of the patient, etc. The closed wound drainage system may be used until closure of the wound occurs or until the patient or clinician opts to use a different type of wound healing device. There is no time limit beyond which use of the closed wound drainage system is no longer beneficial.

There are two possible modes of operation for the application of pressure. One mode involves applying a constant negative pressure, e.g., 125 millimeters of mercury (mm/Hg) below atmospheric pressure. The negative pressure is applied continuously and at the same pressure level as long as the dressing remains on the wound. In the second mode, the negative pressure applied to the wound is modulated within a selected range by supplying air at atmospheric pressure to the wound site (e.g., through a second lumen or tube) to reduce the negative pressure during selected intervals. The vacuum pump remains on at all times so that there is always some level of negative pressure applied to the wound.

The negative pressure produced by the vacuum pump is applied to a wound via the gel cavity which is covered by the porous sheet 324. The porous sheet 324 is attached to the lower surface of the gel 312 to minimize or eliminate the possibility that granulation tissue will prolapse into the cavity, and is made of a material that is specifically designed to be in contact with the open wound surface and not adhere to the wound as it heals. One suitable material for the porous sheet is commercially available under the name "Dermanet" and is a polyethylene non-woven fabric made by DeRoyal Industries in Powell, Tenn.

The gel cavity may be packed with a packing substance 332 which will aid in filtering the exudate that is withdrawn from the wound site and prevent collapse of the wound cavity while negative pressure is being applied. The packing substance 322 is captured between the gel and the porous sheet. The packing substance may be woven organic such as sterile cotton, a non-woven organic such as sterile cotton balls, or a fiberfill. Where a fiberfill is used as the packing substance, the fiberfill may be a porous, fibrous non-woven fiberfill such as a combination of polypropylene and polyethylene. One suitable fiberfill is commercially available under the name "Thinsulate Insulation" and is a fibrous non-woven fiberfill material made by 3M Health Care in St. Paul, Minn. The packing substance may be impregnated with a silver or silver chloride to assist in the healing process.

The gel sheet 312 is preferably covered by a protective material 328 which is attached to the upper surface of the gel. The protective material protects the gel from dirt and liquids that might penetrate into or even through the gel. The protective material may be any medical pressure sensitive adhesive tape which is suitable for adhering to the gel, such as polyurethane tape. Examples of suitable commercially available medical pressure sensitive adhesive tape include "3M™ Medical Foam Tape" available from 3M Health Care in St. Paul, Minn. and "MEDIFIX® 4005" available from Scapa Group PLC in Blackburn, Lancashire in The United Kingdom. The protective material may alternatively, or in addition, incorporate a standard elastogel. The protective material may be permeable to both air and liquid. In the illustrative embodiment, the protective material is roughly the same size as the underlying gel such that little or none of the protective material extends beyond the length of the gel.

It is contemplated that tape may be applied to the protective sheet to assist in securing the closed wound drainage system to the patient's skin surface. This will further aid in keeping the closed wound drainage system attached to the patient's skin surface as well as keeping unwanted substances such as dirt from reaching the open wound.

Prior to application to the patient's skin surface, the lower surface of the gel may be covered with a removable release sheet that assists in protecting the sterility and cleanliness of the gel.

What is claimed is:

1. A closed wound dressing system comprising:
    a layer of moisture permeable gel for application to an upper surface of a wound area and forming a cavity in the gel layer that is open to a wound adjacent to the lower surface of the gel layer, the gel layer being sized to extend beyond the upper surface of the wound area to cover and extend over the wound area without extending into the wound area for attachment to healthy skin outside the wound area, the lower surface of the gel layer adhering to the healthy skin around the wound area without the use of adhesives, the gel layer is permeable to moisture,
    tubing having an inner conduit, a distal end and a proximal end, a distal end portion of the tubing extending into the cavity, the tubing being attached to a gel sealant and extending into the cavity formed in the gel layer,
    a vacuum pump attached to the proximal end of the tubing to apply a negative pressure to the inner conduit,
    a porous material attached to the lower surface of the gel layer extending across an opening to the cavity below the distal end of the tubing without extending into the wound area so that material drawn from a wound into the tubing passes through the porous material,
    a porous packing packed in the cavity in the gel layer without extending into the wound area; and
    a container connected to a proximal end portion of the tubing to accept material drawn into the tubing from a wound.

2. The closed wound dressing system of claim 1 wherein the gel layer is at least one material selected from hydrocolloids, lyogels, hydrogels and self-sustaining, non-flowable, pliable gels having a water soluble humectant entrapped within a polymeric matrix having therein acrylic acid or acrylamide monomer moieties.

3. The closed wound dressing system of claim 1 wherein the gel layer is a self-sustaining pliable gel comprising from about 10 to 25% by weight synthetic polymeric matrix, from about 10 to 50% by weight water, and a substantial quantity of water soluble humectant entrapped within the matrix, the gel layer being characterized by the property of absorbing and desorbing moisture.

4. The closed wound dressing system of claim 1 wherein the gel layer stabilizes temperature in the wound area.

5. The closed wound dressing system of claim 1 wherein the gel layer maintains moisture levels in the wound area and in the healthy skin outside the wound area.

6. The closed wound dressing system of claim 1 wherein the gel layer is impermeable to gas.

7. The closed wound dressing system of claim 1 wherein the gel layer is flexible.

8. The closed wound dressing system of claim 1 wherein the gel layer is capable of forming an airtight seal with the healthy skin outside the wound area.

9. The closed wound dressing system of claim 1 wherein the gel layer is a polymer matrix having a high glycerine content and bacteriostatic and fungistatic properties.

10. The closed wound dressing system of claim 1 wherein the tubing further comprises at least a first lumen and a second lumen, wherein the first lumen applies vacuum pressure to the wound area.

11. The closed wound dressing system of claim 10 wherein the second lumen delivers medication to the wound area.

12. The closed wound dressing system of claim 10 wherein the second lumen provides a path for an electrical line to deliver electrical stimulation to the wound area.

13. The closed wound dressing system of claim 1 wherein the porous packing in the cavity is a woven organic, a non-woven organic, or a fiberfill.

14. The closed wound dressing system of claim 1 wherein the closed wound dressing system is a surface dressing system.

15. The closed wound dressing system of claim 1 wherein the upper surface of the gel layer is covered by a protective material.

16. The closed wound dressing system of claim 1 further including tape for aiding in securing the gel layer over the wound area.

17. The closed wound dressing system of claim 1 wherein the negative pressure modulates from about 1 millimeter of mercury to about 275 millimeters of mercury below atmospheric pressure.

18. The closed wound dressing system of claim 1 wherein the lower surface of the gel layer includes a removable release sheet.

19. The closed wound dressing system of claim 1 wherein the gel layer and the tubing contain an air-tight seal therebetween.

20. The closed wound dressing system of claim 1, wherein the gel layer has a tackiness which is adjustable based on the desired level of adhesion of the gel layer to the healthy skin outside the wound area.

21. The closed wound dressing system of claim 1, wherein the vacuum pump applies negative pressure which is modulated within a selected range.

22. The closed wound dressing system of claim 1 wherein the gel layer is at least one material selected from hydrocolloids, lyogels, and hydrogels.

23. A closed wound dressing system comprising:
  a layer of moisture permeable gel for application to an upper surface of a wound area and forming a cavity in the gel layer that is open to a wound adjacent to the lower surface of the gel layer, the gel layer being sized to extend beyond the upper surface of the wound area to cover and extend over the wound area without extending into the wound area for attachment to healthy skin outside the wound area, the lower surface of the gel layer adhering to the healthy skin around the wound area without the use of adhesives, the gel layer is permeable to moisture, the gel layer comprising a water soluble humectant entrapped within a polymeric matrix having therein acrylic acid or acrylamide monomer moieties,
  tubing having an inner conduit, a distal end and a proximal end, a distal end portion of the tubing extending into the cavity, the tubing being attached to a gel sealant and extending into the cavity formed in the gel layer,
  a vacuum pump attached to the proximal end of the tubing to apply a negative pressure to the inner conduit,
  a porous material attached to the lower surface of the gel layer extending across an opening to the cavity without extending into the wound area so that material drawn from a wound into the tubing passes through the porous material, the porous material covering and extending over the wound area without extending into the wound area,
  a porous packing packed in the cavity in the gel layer without extending into the wound area; and
  a container connected to a proximal end portion of the tubing to accept material drawn into the tubing from a wound.

24. The closed wound dressing system of claim 23 wherein the gel layer stabilizes temperature in the wound area.

25. The closed wound dressing system of claim 23 wherein the gel layer maintains moisture levels in the wound area and in the healthy skin outside the wound area.

26. The closed wound dressing system of claim 23 wherein the gel layer is impermeable to gas.

27. The closed wound dressing system of claim 23 wherein the gel layer is flexible.

28. The closed wound dressing system of claim 23 wherein the gel layer is capable of forming an airtight seal with the healthy skin outside the wound area.

29. The closed wound dressing system of claim 23 wherein the tubing further comprises at least a first lumen and a second lumen, wherein the first lumen applies vacuum pressure to the wound area.

30. The closed wound dressing system of claim 29 wherein the second lumen delivers medication to the wound area.

31. The closed wound dressing system of claim 29 wherein the second lumen provides a path for an electrical line to deliver electrical stimulation to the wound area.

32. The closed wound dressing system of claim 23 wherein the porous packing in the cavity is a woven organic, a non-woven organic, or a fiberfill.

33. The closed wound dressing system of claim 23 wherein the closed wound dressing system is a surface dressing system.

34. The closed wound dressing system of claim 23 wherein the upper surface of the gel layer is covered by a protective material.

35. The closed wound dressing system of claim 23 further including tape for aiding in securing the gel layer over the wound area.

36. The closed wound dressing system of claim 23 wherein the negative pressure modulates from about 1 millimeter of mercury to about 275 millimeters of mercury below atmospheric pressure.

37. The closed wound dressing system of claim 23 wherein the lower surface of the gel layer includes a removable release sheet.

38. The closed wound dressing system of claim 23 wherein the gel layer and the tubing contain an air-tight seal therebetween.

39. The closed wound dressing system of claim 23 wherein the gel layer has a tackiness which is adjustable based on the desired level of adhesion of the gel layer to the healthy skin outside the wound area.

40. The closed wound dressing system of claim 23 wherein the vacuum pump applies negative pressure which is modulated within a selected range.

41. The closed wound dressing system of claim 23 wherein the gel layer absorbs moisture.

* * * * *